United States Patent [19]
Schaffer et al.

[11] Patent Number: 5,821,339
[45] Date of Patent: Oct. 13, 1998

[54] COMPOSITIONS AND METHODS FOR TREATMENT OF HERPESVIRUS INFECTIONS

[75] Inventors: Priscilla A. Schaffer, Holliston; Lily Yeh, Brookline, both of Mass.

[73] Assignee: Dana Farber Cancer Institute, Boston, Mass.

[21] Appl. No.: 458,568

[22] Filed: Jun. 2, 1995

Related U.S. Application Data

[62] Division of Ser. No. 65,146, May 20, 1993, abandoned.

[51] Int. Cl.$^6$ .............................. C07K 16/00; C07K 1/00; C12Q 1/70
[52] U.S. Cl. .......................... 530/387.9; 530/355; 435/5
[58] Field of Search ................................. 530/355, 387.9; 435/5

[56] References Cited

PUBLICATIONS

Baichwal, et al., "Latency Comes of Age for Herpesviruses", Cell, 52, 787–789 (1988).

Batchelor, et al., "Regulation and Cell–Type Specific Activity of a Promoter Located Upstream of the Latency–Associated Transcript of Herpes Simplex Virus Type 1", J. Virology, 64, 3269–3279 (1990).

Bohensky, et al., Identification of a Promoter Mapping within the Reiterated Sequences That Flank the Herpes Simplex Virus Type 1 $U_L$ Region, J. Virology, 67, 632–642 (1993).

Cai, et al., Herpes Simplex Virus Type 1 ICP0 Plays a Critical Role in the De Novo Synthesis of Infectious Virus following Transfection of Viral DNA, J. Virology, 63, 4579–4589 (1989).

Chou, et al., "Mapping of Herpes Simplex Virus–1 Neurovirulence to γ1 34.5, a Gene Nonessential for Growth in Culture", Science, 250, 1262–1266 (1990).

Chou, et al., "The γ1 34.5 gene of herpes simplex virus 1 precludes neuroblastoma cells from triggering total shutoff of protein synthesis characteristic of programmed cell death in neuronal cells", Proc. Natl. Acad. Sci. USA, 89, 3266–3270 (1992).

Davison, A. J., et al., "Nucleotide Sequences of the Joint between the L and S Segments of Herpes Simplex Virus Types 1 and 2", J. Gen. Virology, 55, 315–331 (1981).

DuLuca, et al., "Physical and Functional Domains of the Herpes Simplex Virus Transcriptional Regulatory Protein ICP4", J. Virology, 62, 732–743 (1988).

DeLuca, et al., "Activation of Immediate–Early, Early, and Late Promoters by Temperature–Sensitive and Wild–Type Forms of Herpes Simplex Virus Type 1 Protein ICP4", Mol. Cell. Biology, 5, 1997–2008 (1985).

DeLuca, et al., "Activities of herpes simplex virus type 1 (HSV–1) ICP4 genes specifying nonsense peptides", Nucl. Acid Res., 15, 4491–4511 (1987).

DeLuca, et al., "Isolation and Characterization of Deletion Mutants of Herpes Simplex Virus Type 1 in the Gene Encoding Immediate–Early Regulatory Protein ICP4", J. Virology, 56, 558–570 (1985).

Devi–Rao, et al., "Relationship between Polyadenylated and Nonpolyadenlated Herpes Simplex Virus Type 1 Latency–Asociated Transcripts", J. Virology, 65, 2179–2190 (1991).

(List continued on next page.)

Primary Examiner—Ponnathapura Achutamurthy
Assistant Examiner—Hankyel T. Park
Attorney, Agent, or Firm—Panitch Schwarze Jacobs & Nadel, P.C.

[57] ABSTRACT

A substantially pure preparation of an HSV-specific junction-spanning transcript (L/ST), wherein the 5' end of the L/ST maps to the b repeat sequences of HSV DNA at approximately 3 kb and 125 kb, wherein the L/ST extends into the c repeat sequences of HSV DNA and wherein the HSV DNA sequence encoding the L/ST is preceded by an ICP4 binding site and a TATA box.

14 Claims, 14 Drawing Sheets

PUBLICATIONS

Esparza, et al., "Intertypic Complementation and Recombination between Temnperature–Sensitive Mutants of Herpes Simplex Virus Types 1 and 2", *J. Virology,* 70, 372–384 (1976).

Frankel, et al., "Cellular Uptake of the Tat Protein from Human Immunodeficiency Virus,", *Cell,* 55, 1189–1193 (1988).

Greene, et al., "PC12 Pheochromocytoma Cultures in Neurobiological Research", *Adv. Cell. Neurobiol.,* 3, 373–414 (1982).

Green, et al., "Autonomous Functional Domains of Chemically Synthesized Human Immunodeficiency Virus Tat Transactivator Protein", *Cell,* 55, 1179–1188 (1988).

Hill, et al., "Herpes Simplex Virus Latent Phase Transcription Facilities in Vivo Reactivation", *Virology,* 174, 117–125 (1990).

Honess, et al., "Regulation of Herpesvirus Macromolecular Synthesis", *J. Virology,* 14, 8–19, (1974).

Honess, et al., "Regulation of Herpesvirus Macromolecular Synthesis: Sequential Transition of Polypeptide Synthesis Requires Functional Viral Polypeptides", *Proc. Natl. Acad. Sci. USA.,* 72, 1276–1280 (1975).

Imbalzano, et al., "Functional Relevance of Specific Interactions between Herpes Simplex Virus Type 1 ICP4 and Sequences from the Promoter–Regulatory Domain of the Viral Thymidine Kinase Gene", *J. Virology,* 64, 2620–2631 (1990).

Jones, et al., "Transacting protein factors and the regulation of eukaryotic transcription: lessons from studies on DNA tumor viruses", *Genes & Dev.,* 2, 267–281 (1988).

Jones, et al., "A Cellular DNA–Binding Protein that Activates Eukaryotic Transcription and DNA Replication", *Cell,* 48, 79–89 (1987).

Krause, et al., "Detection and Preliminary Characterization of Herpes Simplex Virus Type 1 Transcripts in Latently Infected Human Trigeminal Ganglia", *J. Virology,* 62, 4819–4823.

Leib, et al., "Immediate–Early Regulatory Gene Mutants Define Different Stages in the Establishment and Reactivation of Herpes Simplex Virus Latency", *J. Virology,* 63, 1757–768 (1989).

Leib, et al., "A Deletion Mutant of the Latency–Associated Transcript of Herpes Simplex Virus Type 1 Reactivates from the Latent State with Reduced Frequency", *J. Virology,* 63, 2893–2900, (1989).

McCarthy, et al., "Herpes Simplex Virus Type 1 ICP27 Delection Mutants Exhibit Altered Patters of Transcriptional and Are DNA Deficient", *J. Virology,* 63, 18–27 (1989).

McGeoch, et al., "Sequence Determination and Genetic Content of the Short Unique Region in the Genone of Herpes Simplex Virus Type 1", *J. Mol. Biology,* 181, 1–13 (1985).

McGeoch, et al., "Comparative sequence analysis of the long repeat regions and adjoining parts of the long unique regions in the genomes of herpes simplex viruses types 1 and 2", *J. Gen., Virology,* 72, 3057–3075 (1991).

Meek, et al., "Inhibition of HIV–1 protease in infected T–lymphocytes by synthetic peptide analogues", *Nature,* 343, 90–92 (1990).

Mitchell, et al., "Mapping of low abundance latency–associated RNA in the trigeminal ganglia of mice latently infected with herpes simplex virus type 1", *J. Gen. Virology,* 71, 125–132 (1990).

Murchie, et al., "DNA Sequence Analysis of an Immediate–Early Gene Region of the Herpes Simplex Virus Type 1 Genome (Map Coordinates 0.950 to 0.978)", *J. Gen. Virology,* 62,1–15 (1982).

Sacks, et al., "Deletion Mitants in the Gene Encoding the Herpes Simplex Viruse Type 1 Immediate–Early Protein ICP0 Exhibit Impaired Growth in Cell Culture", *J. Virology,* 61, 829–839 (1987).

Sacks, "Herpes Simplex Virus Type 1 ICP27 is an Essential Regulatory Protein", *J. Virology,* 55, 796–805 (1985).

Schaffer, et al., "Collaborative Commplementation Study of Temperature–Sensitive Complementation Study of Temperature–Sensitive Mutants of Herpes Simplex Virus Types 1 and 2", *J. Virology,* 490–504 (1978).

Smiley, et al., "The Herpes Simplex Virus Type 1 (HSV–1) a Sequence Serves as a Cleavage/Packaging Signal but Does Not Drive Recombinational Genome Isomerization When it is Inserted into the HSV–2 Genome", *J. Virology,* 66, 7505–7510 (1992).

Spivak, et al., "Detection of Herpes Simplex Virus Type 1 Transcripts during Latent Infection in Mice", *J. Virology,* 61, 3841–3847 (1987).

Stevens, et al., "RNA Complementary to a Herpesvirus α Gene mRNa is Prominent in Latently Infected Neurons", *Science,* 235, 1056–1059 (1987).

Trousdale, et al., "In Vivo and In Vitro Reactivation Impairment of a Herpes Simplex Virus Type 1 Latency–Associated Transcript Variant in a Rabbit Eye Model", *J. Virology,* 65, 6989–6993 (1991).

Wagner, et al., "The Herpes Simplex Virus Latency–Associated Transcript is Spliced during the Latent Phase of Infection", *J. Virology,* 62, 4577–4585 (1988).

Weller, et al., "Genetic Analysis of Temperature–Sensitive Mutants which Define the Gene for the Major Herpes Simplex Virus Type 1 DNA–Binding Protein", *J. Virology,* 45, 354–366 (1983).

Zwaagstra, et al., "Activity of Herpes Simplex Virus Type 1 Latency–Associated Transcript (LAT) Promoter in Neuron–Derived Cells: Evidence for Neuron Specificity and for a Large LAT Transcript", *J. Virology,* 64, 5019–5028 (1990).

Baichwal V et al, Latency comes of age for herpesvirus, Cell 52:787–789, Mar. 1988.

Stevens J et al, RNA complementary to a herpesvirus alpha gene mRNA is prominent in latently infected neurons, Science 235:1056–1059, Feb. 1987.

Farrell M et al, Herpes simplex virus latency–associated transcript is a stable intron, Proc. Nat'l Acad. Sci. 88:790–794, Feb. 1991.

Doerig C et al, An antigen encoded by the latency–associated transcript in neuronal cell cultures latently infected with herpes simplex virus type 1, J. Virol. 65(5):2724–2727, May 1991.

Cheung A et al, Cloning of the latency gene and the early protein O gene of pseudorabies virus, J. Virol. 65(10):5260–5271, Oct. 1991.

Vlcek C et al, Pseudorabies virus immediate–early gene overlaps with an oppositely oriented open reading frame: Charaterization of their promoter and enhancer regions, Virol. 179:365–377, 1990.

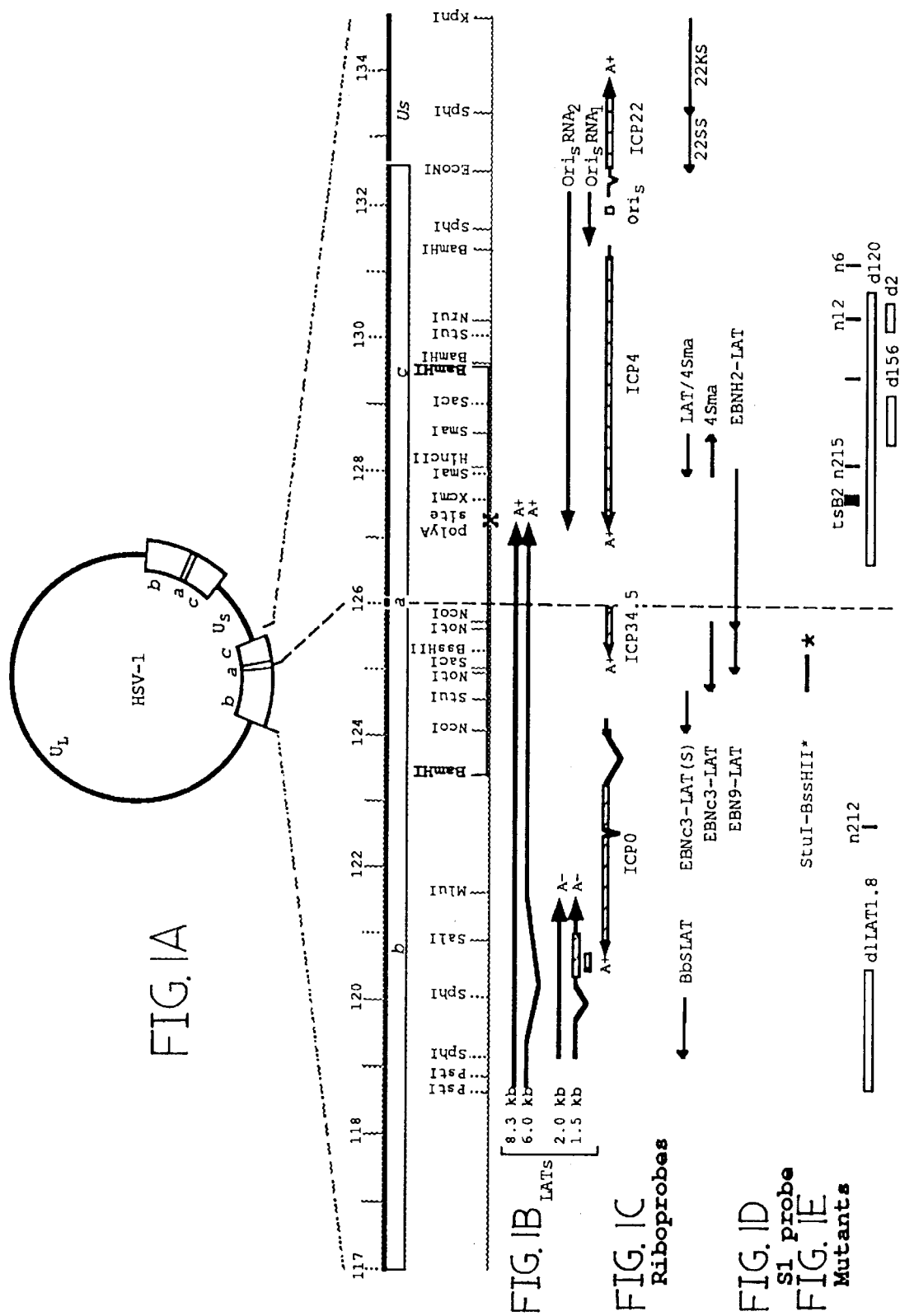

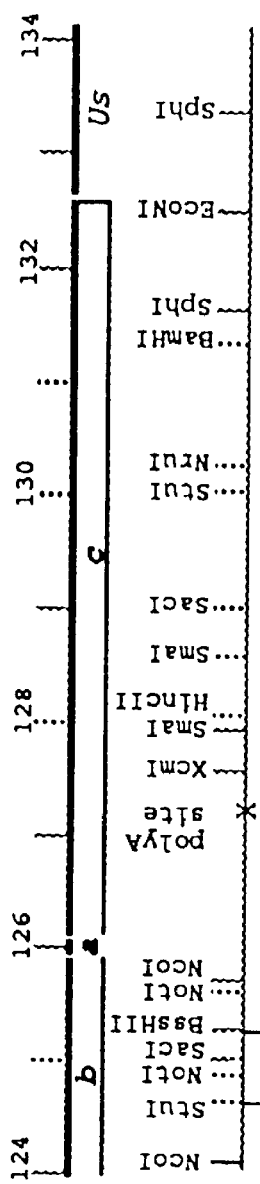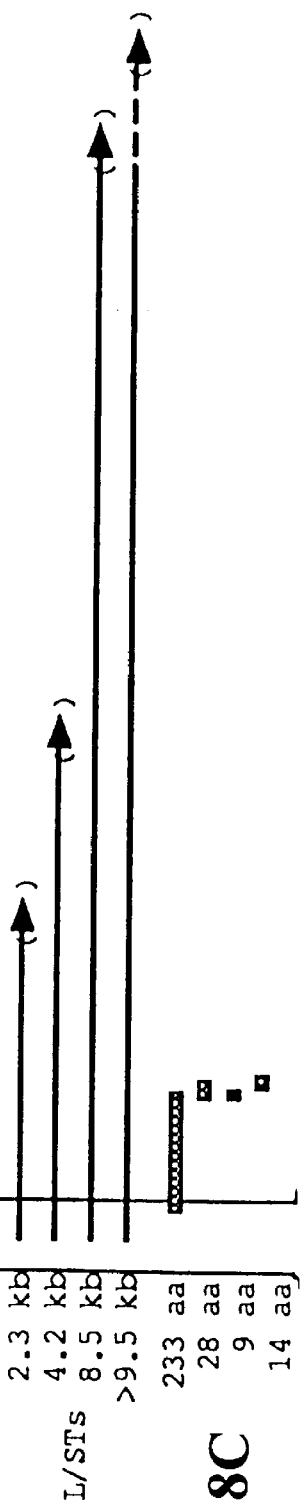
Fig. 8A
Fig. 8B
Fig. 8C

Fig. 8D

```
     StuI                                                  E4TF1
AGGCCTCTTG CAAGTTTTTA ATTACCATAC CGGAAGTGG GCGCCCCGCCC AGTGGGCGGT AGTTACCGCC CAGTGGGCCG GCCCGAAGAC  100
                                        NotI          MscI
TCGGGGGACG CTGGTTGGCC GGGCCCCGCC GGCGCTGGCGG CCGCCGATTG GCCAGTCCCG CCCCCGAGGC GGCCCCGCCCT GTGAGGGCGG  200
                                    ICP4 binding
                                                                        SacI
GCTGGCTCCA AGCC TATATA T GCGCGGCTC CTGC ATCGT CTCTCCGGAG AGGGGCTTGG TGCGGAGCTC CCGGGAGCTC CGCGGAAGAC  300

SacI
CCAGGCCGCC TCGGGTGTAA CGTTAGACCG AGTTCCGCCG GCCGCTCCG CGGGCCAGGG CCCGGGCACG GGCCTCGGGC CCCAGGCACG  400

BssHII
GCCCGATGAC CGGCCCGGCC TCCGGCCACCC GGGCCGGGAA CCGAGCCCCGG TCGGCCCCGCT CGGTGGCCCCA CGAGCCCGGG CGCGC
```

Fig. 9A

```
1184/1
ATG ACC GCC TCG GCC TCC GCC ACC CGG CGC CGG AAC CGA GCC CGG TCG GCC CGC TCG CGG
 M   T   A   S   A   S   A   T   R   R   R   N   R   A   R   S   A   R   S   R
1244/21
GCC CAC GAG CCG CGG CGC CGG AGG CGG GCG GCC GAG GCC CAG ACC ACC AGG TGG CGC ACC
 A   H   E   P   R   R   R   R   R   A   A   E   A   Q   T   T   R   W   R   T
1304/41
CGG ACG TGG GGC GAG AAG CGC ACC CGC CGC GCG GGG GTC GCG GGG GTC AGG CGC GGG
 R   T   W   G   E   K   R   T   R   R   A   G   V   A   G   V   A   G
1364/61
GTC GCG GGG GTC GCG GGG TCC GGC GGG AGC CTC CCG CCC GGG CGT AGG CGC AGG
 V   A   G   V   A   G   S   G   G   S   P   P   P   G   R   R   R   R
1424/81
CGC GCC AGG TGC TCC GTG ACG CGC AGG GCG AGG GCG CGC GAG CGC GGA AGG CGG AAG
 R   A   R   C   S   V   T   R   R   A   R   A   R   R   G   R   R   K
1484/101
GGG CGC GAG GGG TGG GAG GGG TCA GCC CCC CCC GGG CCC ACG CCG GGC GGT GGG
 G   R   E   G   W   E   G   S   A   P   P   P   G   P   T   P   G   G   G
1544/121
GGC CGG GGG GCG GCG GCG GTG GGC GCG AGG GCG GCC TCT GGC GCC GAC TCG GGC GGG GGG
 G   R   G   A   A   A   V   G   A   R   A   A   S   G   A   D   S   G   G   G
1604/141
CTG TCC GGC CAG TCG TCG TCA TCG TCG TCG GAC GCG GAC TCG GGA ACG TGG AGC CAC
 L   S   G   Q   S   S   S   S   S   S   D   A   D   S   G   T   W   S   H
1664/161
TGG CGC AGC AGC AGC GAA CAA GAA GGC GGC CCA CCG GGC GGC GGC GGC GGC GGC GCG
 W   R   S   S   S   E   Q   E   G   G   P   P   G   G   G   G   G   G   A
1724/181
GGC CGG GGG GCG GCG CTC CTG ACC GCG GGC TTG GGC GTG GAG GTT ACC CGG GGG GCG
 G   R   G   A   A   L   L   T   A   G   L   G   V   E   V   T   R   G   A
1784/201
GCG GTT GGG ACG GCG CCC GTG GGC CCG GGC CGG CGG CCG CGA TGG GAC TGT
 A   V   G   T   A   P   V   G   P   G   R   G   R   R   P   R   W   D   C
1844/221
CGG CGG CGG GCC ATG GAG ACA GAG AGC GTG CCG GGG TGG TAG
 R   R   R   A   M   E   T   E   S   V   P   G   W   *
```

Fig. 9B

```
1837/1
ATG GCG GCG GCG GCG GGC CAT GGA GAC AGA
 M   A   A   A   A   G   H   G   D   R

1867/11
GAG CGT GCC GGG GTG GTA GAG TTT GAC AGG
 E   R   A   G   V   V   E   F   D   R

1897/21
CAA GCA TGT GCG TGC AGA GGC GAG TAG
 Q   A   C   A   C   R   G   E   *
```

Fig. 9C

```
1856/1
ATG GAG ACA GAG AGC GTG CCG GGG TGG TAG
 M   E   T   E   S   V   P   G   W   *
```

Fig. 9D

```
1902/1
ATG TGC GTG CAG AGG CGA GTA GTG CTT GCC
 M   C   V   Q   R   R   V   V   L   A

1932/11
TGT CTA ACT CGC TAG
 C   L   T   R   *
```

Fig. 10A

```
             10         20         30         40         50         60         70         80
             |          |          |          |          |          |          |          |
  815                   AGGCCT CTTGCAAGTT TTTAATTACC ATACCGGGAA GTGGGGCGCC CGGCCCATTG GGCGGTAACT  880
  881 CCCGCCCAAT GGGCCGGGCC CCGAAGACTC GGGGACGCT GCCCCGCCGC GTTGGCCGG GCCCCGCCGC GCTGCCGGCC GCCGATTGGC  960
  961 CAGTCCCGCC CCGAGGCGG CCCGCCCTGT GAGGGCGGGC TGGCTCCAAG CGTATATATG CGGGCTCCT GCCATCGTCT 1040
 1041 CTCCGGAGAG CGGCTTGGTG CGGAGCTCCC GGAGCTCCG CGGAAGACCC AGGCCGCCTC GGTGTAACG TTAGACCGAG 1120
 1121 TTCCCGGGC CGGCTCCCG GGCCAGGGCC CGGCAGGGG CCTCGGGAC CAGGCACGC CCGGGTCGC CCTCGGCCTC 1200
 1201 CGGCACCCGG CGCCGGAACC GAGCCCGTC GGCCCGCTCG CGGGCCCACG AGCCGCGGCG CGCCAGGCGG GCGGCCGAGG 1280
 1281 CCCAGACCAC CAGGTGGCGC ACCCGGACGT GGGGCGAGAA GGGCACCCG GGGGGGTCG CGGGGGTCGC GGGGTCGCG 1360
 1361 GGGGTCGCGG GGGTCGCGGG GGGCTCCGGC GCCCCTCCC CGCCCGGGCG TGCAGGCGC AGGCGGCGCA GGTGCTCGGC 1440
 1441 GGTGACGCGC AGCGGAGG CGAGGCGCCG CGGAAGGCG AAGGGGCGG AGGGGGGTG GAGGGGTCA GCCCGCCCC 1520
 1521 CCGGGCCCAC GCCGGCGGT GGGGCGCGG CGGGGGGGC GCGGGGCGTG GGCGGGCT CTGGGCGCA CTCGGGCGGG 1600
 1601 GGGCTGTCCG GCCAGTCGTC GCCGTGGACG CGGACTCGGG AACGTGGAGC CACTGGGCA GCAGCAGCGA 1680
 1681 ACAAGAAGC GGGGCCCCAC CGGCGGCGG GGGCCGCCCG GGGGCTCCT GACCCGGGGT TCCGAGTTGG 1760
 1761 GGTGGAGGT TACCTGGGAC TGTGCGGTTG GACGCGCCC CGTGGGCCC CGTGGGCGGG GGGCGGGGG GCGCGGATGG 1840
 1841 CGGCGGGGGC GGGCCATGGA GACAGAGAGC GTGCCGGGGT GGTAGAGTTT GACAGGCAAG CATGTGCGTG CAGAGGCGAG 1920
 1921 TAGTGCTTGC CTGTCTAACT CGCTAGTCTC GGGGCTGGGG GGCGGCTGGG GCCGGGGCT GCCCGGGCC ACCGCTTTAA AGGGCCGGC 2000
 2001 GCGACCCCCG GGGGTGTGT TTTGGGGGG GCCCGTTTC GCCGGTCTGGC CGTCCTCCC ACCGCTCCTC CCCCGCTCTC 2080
 2081 CCTCCCCGT CCTTCCCCG CCTCCTCCC CGCTCCTC CCCGGCTCC TCCCCCGCT CTCCTCCCC CCTCCCCCG CCTCCCCG 2160
 2161 CTCCTCCCCC CGTCCTCCC CCCCGCTCC CGCTCCTCC CCCCCGCT CTCCTCCCC GCCCGCACG CGGCGCACG CGCTCCTCCC 2240
 2241 CCCGGCTCC CCCCGCCCGG CGCGGCGGG CCCCGGGGG CCCCGCCCC GCGGCGGG GCCGCGCCG CCCCGGAC 2320
 2321 CGCGGCCCGC CTTTTTGCG GCGGGGGGG CCCCGGGGG CCCGCGGGG CCACAGGTGA AACCAACAGA GAACGGCGCA 2400
 2401 CTCCACACGT CACACGTCAC GTCATCACC ACACCTGCCC AACACACAGA CTCACAGCGA CAACTCACCG CGCAACAACT 2480
 2481 CCTGTTCCTC ATCCACACGT CACCGCGCAC CTCCCGCTCC CCCGGGCGCA ACACACGCT CCTGCTACAC AGGGCCGGC 2560
 2641 CGGGCCCAGC CCTTCGGGGA GGTTCGGGCA AGTGCGCCA CCCAGCGCC AGAGATCCAA GCCCCCAGCC GTCCCGCGCT GGGGCCCGG 2720
 2721 CCCTCGGGG GGTTCGGGCA AGTGCCGCCA TCTCAGTC AGTGCGCCA AGAGATCCAA ACCCTCCGGG GGGGCCCGG CCCTCCCGC 2800
 2801 CACCACCAC GCCCCTCGC CCTTCGCCCG CCTCGCCC CCTCGCCCC TCCCGCCCC CGCCCTCGCC CCCTCGCCC CCCTCCCGC 2880
 2881 CCCTCGCCCC CTCCGCCCTC TGCCCCCTCG CCGCCCCTCG CCCCTCGC CCCCTCGCCC CTCCCCGCC CTCGCCCCT 2960
 2961 CCCGCCCCT GCCCCTCGCC CCCCTCGCC CTCGCCCT CCCCCTCGCC CCCTCGCCC CCCTCGCCC CCCCTCGCC CGCCCCTCGC 3040
 3041 CCCTCCCGG CCCTCGCCC CCTCCCGCC TGCCCCCTC CCCCTCCCG CCCTCCCCC CCTCCCCG CCCCCTCCCC CTCCCGCGC 3120
 3121 CTCGCCCCT CTCGCCCCT GAATAAACAA CGTACTGCA AGTTGTTGC CGTTTATTGC GTCTTCGGGT 3200
 3201 CTCACAAGCG CCCGGCCCCG TCCGCAACCG TTACAGCACC CGGGGCGCC GCGTCGTCT TGTCCAAGG 3280
```

Fig. 10B

| | | | | | |
|---|---|---|---|---|---|
| 3281 | CGCCTTCCCA | GTCCACAACT | TCCCGCGCCG | GGGGCGTGGC | CAAGCCCGCC | TCCGCCCCCA | GCACCTCCAC | GGCCCCCGCC | 3360 |
| 3361 | GGCCAGCA | CGGTGCCGCT | GGCCCCCGTG | GCCGAGGCC | AGGGAATCCC | GGGCGGGGCC | GGCCCAGGG | CCCCGGGGCC | 3440 |
| 3441 | GTCGTCGTCG | CCGGCCAGCA | CCAGCGGGGG | GGCGTCGTCG | TCGGGCTCCA | GCAGGGGGCG | GGCGCAAAAG | TCCCTCCGCG | 3520 |
| 3521 | GCCCAGCGCA | CCGGGCCGGA | CCAGCGCGGA | CCGGCCTCGG | CCCCAGCGCC | AGTACACGG | GCCCAGCGCG | CGGGCCCAGG | 3600 |
| 3601 | CCCCAGCGCG | CGCAGGCGGC | GTGGAGTGG | CGCCCTCCT | GCCAGAAGTC | CGGCGCGCGG | GCCGCCATGG | CGTCGTGGT | 3680 |
| 3681 | CCCCGAGGCC | GCCGCCCGGC | CGTCCAGCGC | GGCCAGCACG | GCCGGCGCGT | ACTCGCGCGG | GGACATGGGC | ACCGGCGTGT | 3760 |
| 3761 | CCGGGCCGAA | GCCGTGCGC | ACGGGTAGC | CGGCAGCACG | GCCGGCCAC | AGGCCAGCG | GGGCGGGGTC | GGGTACAGG | 3840 |
| 3841 | CGGCCGTGCG | CGGCCTCCAC | GCGGCAGCA | ACCCCGGCC | CGAACACGCG | GCCGAGGCC | GGGCGGTGC | GGCGCAGGTC | 3920 |
| 3921 | CCGCGCCGC | GCGCAGCGCA | CGGGCGGGG | TCGCAGGCGC | AGCAGCTCGC | ACGCCAGTA | AGCACCGTGC | CCGACACCG | 4000 |
| 4001 | CGGGCCCGTC | GGGGGCCAG | TCGCAGGCGC | GCACGGTGTT | GACCACGATG | AGCCGCGCGT | GGCGTGCTGC | GGCGAGCAGC | 4080 |
| 4081 | CCCAGAAACT | CCACGCCCCC | GGCGAAGGCC | AGTCCCGCG | TGGACAGCAG | CAGCACGCCC | GCCCGCGCT | GGCGAGCACAC | 4160 |
| 4161 | GTCGGGGCG | CCGGTCCAAT | TGCCCGCCCA | GGGCGCGTG | TCCGCCCGCG | ACAGCCGGTT | GGCCAGGGCC | GCCAGCAGGC | 4240 |
| 4241 | AGGACAGCCC | GCCGCGCTCG | GCGACCACT | CCGGACCACG | GCGACACGG | CGGCACGCGG | CCAGTCCTC | GCCGGCCAGC | 4320 |
| 4321 | GGCGAGTACA | GCACCACCAC | GGCACGTCC | TCGGGGTCGG | CCCCGAGGCC | GATCTGGG | CATCCAGGCC | GCCATGGGCC | 4400 |
| 4401 | CGAGGCGCG | AGGGGCCAA | AGAGGCGGCC | CCCGGGGCG | CCGTGGGGT | CCGTGGTGC | GGGGTTATC | GTCGTGTCG | 4480 |
| 4481 | ACGGGGCCTG | GGGCGGGGG | GCCGGGGGG | GGCCGGGG | GCGGATCGAG | GCCAGGCCCC | GGGGTCAAA | CATGAGGCC | 4560 |
| 4561 | GGTCGCCAGG | GGACGGGGAA | CAGCGGGTGG | TCCGTGAGCT | CGGCGCCAGG | GGGGGGAG | CAGTAGGCT | CCAGGCGGC | 4640 |
| 4641 | GGCCGCGGGC | GCCGCCCGTGT | GGCTGGGCCC | CGGCGGCC | GGGAGCTCGG | CAGGCCAGG | GTCGGGGCCC | TCGGCGGCC | 4720 |
| 4721 | GGGCGGACAC | GGCCACGGG | CACGCGGGG | CCTGCGCCC | ACGGCGGCCT | CGTGCGCC | GGCACGCGC | AGTCCCGCG | 4800 |
| 4801 | GGGCCCGGGG | GGGTGGAGGG | GGCGCGGGC | GCGGGGAGGG | CTCGCGCCA | CGAACCGCAG | GCCTGCGCC | GGCGGGGC | GTCGGCGTGC | 4880 |
| 4881 | CTTCGTCTTC | GGGGGTCGCG | GGCCGGGGC | TCCGGGGGG | GGGGGCGGC | CGGGGGGT | GTCCGAGCCG | CGCCGCTCTT | 4960 |
| 4961 | GCGCGGGGA | GGGCGGGCG | GCCGGGGCG | GGCCAGGGGG | CGGGCAGCAG | CGGGACTCTT | GGCTTGCGC | CCCTCCCGG | 5040 |
| 5041 | CTCTGGTTGT | CAAACAGCAG | GTCCGCGGGG | GGCCAGCGCG | GTCGGTGCG | CTGGCGCAG | CGGCCAGCAG | GGGGCGCAGG | 5120 |
| 5121 | CAGGGCCCCG | GGACCAGC | TCACGGGGG | GGGAGCTCGG | GGCGGGGCC | CAGGCGGGGG | TCCCGGGGCA | GCCGGGGCC | 5200 |
| 5201 | GCAGCGCAT | GAGCACCAGC | GGGTCGCGCA | GGTCGCGCA | CTCGCCGCAG | GCCTGCGCC | CACGCGGCA | AGTCCCGCG | 5280 |
| 5281 | GGCGGGGCG | GGAAGCGGG | GCCCGGGGT | GGGCCCTCGG | CGAACCGCAG | CCCTCCGGG | GGCAGGCGCA | GTCGCGTGC | 5360 |
| 5361 | GGCGGCCAGG | TCGCCGTCGA | AGCCCTCGGC | CAGGCGCTCC | CAGCGCTTCG | CAGCGCCGCG | GCAGGCGGC | GGCCCGGGAC | 5440 |
| 5441 | GGCCGGCCTG | GGCGGCGGC | CGGCGTCGT | CGGCGAGGAT | CGTCGGGCC | AGGATCCCGC | CAGGCACTCG | ACGGCCACCG | 5520 |
| 5521 | GAGGCGGGGC | CGGCGGACAG | CGGCGACGCC | CGGCGTGCGC | GGCGAGGCC | CCCCAGGGG | GGCAGGCGGC | CCCCGGGGG | 5600 |
| 5601 | GGTGCGGGGG | TCGCCGGCGC | CGGACCCCC | CGGCGTCCCC | CGGCCTGCGCC | CGTACCCGG | GGTCGTCGCC | GGCTCGCGC | 5680 |
| 5681 | GTTCTCGCGG | GCCAACAGGG | GCCGTAGCC | GGGCGCAGG | CTGGTCAGCA | GAAGCCCTT | CTGCGCCGCG | TCGTATCGGC | 5760 |

Fig. 10C

```
5761 GGCTCATGGC CACGGCGGGCC GCCGCGTGCG CCAGGCCCCA GCCGAAGCGG CCGGCCGCCA TGGCGTAGCC CAGGTGGGGC 5840
5841 ACGGCCCGCG CCACGCTGCC GGTGATGAAG GAGCTGCTGT TGCGCGGCGC GCCCCGAGATC CGAAGCAGG CCTGGTCCAG 5920
5921 CGCCACGTCC CCGGGACCA CGCGCGGGTT CTGGAGCCAC CCCATGGCCT CCGCGTCCGG GGTGTACAGC AGCCGCGTGA 6000
6001 TCAGGGCGTA CTGCTGCGCG GCGTCGCCCA GCTCGGGCGC CCACACGGCC GCCGGGGCGC CCGAGGCCTC GAACCGGCGT 6080
6081 CGCGCCTCCT CCGCCTCGGG CGCCCCCCAG AGGCCCGGGC GGCTGTCGCC CAGGCCGCCG TACAGCACCC GCCCGGGGG 6160
6161 CGGGGGCCCG GCGCCGGGCC ACGGCTCCCC GCTGACGTAC AGCGCGCGTA GAAGGCGCCG GAGGTCGCGT 6240
6241 CGGCGTCCAG CTCGACCCGC CGGGGCTGCC CGGGCCGTGA CCGTCGCGAT GCGGCCCGTG GCTCGGCGC            6??0
6321 CGGCGGCGCT CGATGCGGCC CGCGGAGGCC GCGGGGGTCC TGCGCGCGC CGGGGGCTTG GGCGCGGCCT CGGAGAGGGG GCCCGCGCT 6480
6401 GGTGGCCCG GGCGGGGGCG GGTCCGCCC GGGGCTGCC TCGACGGACC CCGCCCGACG TGCGGACGAC 6560
6481 CGCGTGCGTG GTCGGCCCGG TCGTTGCCGT CGTTGTCCTC GTCCTCGTCG GACGACGAGG ACGAAGAGGA GCGGGCGCTG 6640
6561 GAGGACAGAG ACCCGGAGTC CGACGAGTC GATGACGCCG ATGGCCCGCA CCGGCCGTGA CGAGTCTCC GCGGGGGCTG 6640
6641 GGCCGGCGGG CGCGGCGACA GGCGGTCCGT GGGGTCCGGA TACGCGGCGC GTAGGGGGC CTCCCGTTCG CGGCCCCCGG GGCGGGTC 6720
6721 CGGGGCCCG GTCGCCGGGG GGTCGGGCTG CGTCGTCGTA CTCGTCCCCG TCATCGTCGT CGGCTCGAAA GGCGGGGTC ??? 6800
6801 CGGGGCGGCG AGGCCGGCGG GTCGGGGCGTC GGATCGTCC GGACGGCCTC CTCTACCATG GAGGCCAGCA GAGCCAGCTG 6880
6881 TCGCGCGAG ACGGCGTCCC CGGGCGTCTC CCCGGCGTCG GTGCCCGCG CCCGTCCCGC CCGTCCCCGC CGGGCGTCGT 6960
6961 CGAGGTCGTG GGGGTGGTG GGGTCGTGGT CGGGGCCCGC CCGCCCTCCG TCCGTCTCCG CGCCCCACCC GAGGGCCCCC 7040
7041 CGCTCGTCGC GGTCTGGGCT CGGGGTGGGC CGGGTGGGC GCGCCCGT CGGGAGCCG GGGCGCTGCT TGTTCTCCGA 7120
7121 CGCCATCGCC GATGGGGGGC GATCCTCCGG GGATACGGCT GCGACGGGGG ACTAGCACG GTAGTCACC TACGGACTCT 7200
7201 CGATGGGGGG AGGGGCGGAG ACCCACGGAC ACCCACGGAC CCCGCGTCG ACGGGAACT AGCGGGACC GGTCGATGCT 7280
7281 TGGGTGGGAA AAAGGACAGG GACGGCCGAT CCCCCTCCCG CGCTTCGTCC GGTATCGGC GTCCGGGGGC GCCGAGCGTC 7360
7361 TGACGGTCTG TCTCTGGGGG GGTCGTGGT TCCCGCGTCG GTCGTGGAT CCGTGTCGGC AGCCGCGCTC CGTGTGACG ATGGGGGGT 7440
7441 CCTCGGGCTC ATATAGTCCC AGGGGGCCGG GGAAGAGG ACCAGCGGAA GCCGCCGCC CCCCCCCC CCGGCGGGCC 7520
7521 CACCCGAAC GAATTCCAT TATGCACGAC CCCGCCCGA CGGGGCACG CGGGGCGAG GCCGCGCC GTGCCGCGG CCCGTTGGTC 7600
7601 GAACCCCG CCCCGCCAT CCGCCGCAT TGCCATGGC GGGGGCGAG GGGGGTGGG TCCGCGCCC GCCCCATG 7680
7681 GCATCTCATT ACCGCCGAT CCGGCGTTT CCGCTTCCGT TCCCATGCT AACGAGAAC GGGCAGGGGG CGGGGCCCGG 7760
7761 GCCCGGACTT CCCGGTTCGG CGGTAATGAG ATACGAGCCC GCCGCCCCG TTGCCGTCC CCGGCCCCC CGTTCCCGCC 7840
7841 CGCCGGACGC GGGGACCAAC GGGACGCGG GCGGCCCAAG GCGCCCGCC CTTGCCCCC CCCATTGGC CGGGGCCGC 7920
7921 GACCGCCCCA AGGGGCGGGG GCCGCCGGGT AAAAGAAGTG AGAACGCGAA GCGTTCGCAC TTCGTCCAA TATATATATA 8000
8001 TTATTAGGGC GAAGTGCGAG CACTGCGCC CCGCCCGACT CCGCAGACGG CCCCGGGGCG GCCGGGCC GGGGGGGCG 8080
8081 GGTCTCTCCG GCGCACATAA AGGCCCGGCG CACCGACGCG CGCCAGACGG GAACGACGG AGCGGCTGCG 8160
8161 GAGCACGCGG ACCGGGAGCG GGAGTCGCAG AGGGCCGTCG CGTCGGCATC GCGACGCCCC GGCTCGGGAT 8240
```

Fig. 10D

```
8241  CGGGATCGCA TCGGAAAGGG ACACGCGGAC GGGGGGGGGA AAGACCCGCC CACCCCACCC ACGAAACACA GGGGACGCAC  8320
8321  CCCGGGGGCC TCCGACGACA GAAACCCACC GGTCCGCCTT TTTTGCACGG GTAAGCACCT TGGGTGGGCG GAGGAGGGCG  8400
8401  GGACGCGGGG GGGGAGGAGG GGGGACGCGG GGGCGGAGGA GGGGGACGCG GGGGGCCGAG GGGGGGGAC GCGGGGGCGG  8480
8481  AGGAGGGGGG ACGCGGGGGC GGAGGAGGGG GCTCACCCGC GTTCGTGCCT TCCCCAGGA GGAACGTCCT CGTCCAGCCG  8560
8561  ACCGGGGCCG ACCGTTGCGT GGACCCGCTC CTGCTCGTCG GCGGGGGGA AGCCACTGTG GTCCTCCGGG AGTTTTCTG  8640
8641  GATGCCGAC ATTTCCCCAG GCGCTTTTGC GCCTTGTGTA AAACGCGGC GTCCCGCTCT CCGATCCCG GTCTGAGGTC  8720
8721  CGCGCAAGCG CAAGCGCCCT TCCCGCCCCC TCTCATCGGA GTCTGAGGTA GAATCCCATA CAGCCTTGA GTCTGAGGTC  8800
8801  GAATCCCAGA CAGCATCGGA TTCGACCGAG TCTGGGACCC AGATGAAGC CCCCCGATC GGTGGCCGTA GGGCCCCCG  8880
8881  GAGGCTTGGG GGGCGGTTTT TTCTGGACAT GTCGGCGAAA TCCACCACGG GGACGGAAAC GGATGCGTCG GTGTCGGACG  8960
8961  ACCCCGACGA CACGTCCGAC TGGTCTTATG ACGACATTCC CCACGACCC AAGCGGGCCC GGGTAAACCT GCGGCTCACG  9040
9041  AGCTCTCCCG ATCGGCGGGA TGGGGTTATT TTTCCTAAGA TGGGGGGGT CCGGTCTACC CGGAAACGC AGCCCCGGGC  9120
9121  CCCACCCCCG TCGGCCCCAA GCCCAAATGC AATGCTACGG CGCTCGGTGC GCCAGGCCCA GAGGCGGAGC AGCGCACGAT  9200
9201  GGACCCCCGA CCTGGGCTAC ATGCGCCAGT GTATCAATCA GCTGTTTCGG GTCCTGCGGG TCGCCCGGGA CCCCCACCGC  9280
9281  AGTGCCAACC GCTGCGCCA CCTGATACGC GACTGTTACC TGATGGGATA CTGCCGAGCC CGTCTGCCCC CGCGCACGTG  9360
9361  GTGCCGTTTG CTGCAGGTGT CCGGCCGGAAC CTGGGCCATG CACCTGCGCA ACACCATACG GGAGGTGGAG GCTCGATTCG  9440
9441  ACGCCACCGC GGAACCCGTG TGCAAGCTTC TGGGGTTTGA GACCAGACGG TACGGCCCCG AGTGTGATCT TAGTAATCTC  9520
9521  GAGATTCATC TCAGCGCGAC AAGCGATGAT GAAATCTCCG ATGCCACCGA TCTGAGGCC GCCGTTGCGG ACCACACGCT  9600
9601  CGCGTCCCAG TCCGACACGG AGGATGCCCC CTCCCCCGTT ACGGTTGAAA CCCCAGAACC CGGGGGTCC CTCGCTGTGC  9680
9681  GTCTGGAGGA TGAGTTTGGG GAGTTTGACT GGAGGCTCC CAGCCCCTGGC TGTCTGCGGT CGTGGCCGAT  9760
9761  ACCAGCTCCG TGGAACGCCC GGGCCCATCC GATTCTGGGG CGGGTCGCGC CGCAGAAGAC CGCAAGTGTC TGGACGCTG  9840
9841  CGGAAAATG CGCTTCTCCA CCGCTCGTCC CTATCCGTGC AGCGACACGT TTCTCCGGCG GTGAGTCCGG TGCCCCCGAC  9920
9921  CCCCTTGTAT GTCCCCAAAA TAAAAGACCA AAATCAAAGC GTTTGTCCA GGGTCTTAAT GCCGGGAAGG GCGAGAGAA  10000
10001 ACAGACCACG CGGACATGGG GGGTGTTTGG GGGTTTATTG CCACCGGGGG CTAAAGGGTG GTAACCGGAT AGCAGATGTG  10080
10081 AGGAAGTCGG GGCCGTTCGC CGCGAACGGC GATCAGAGGG TCAGTTTCTT GCGGACCACG GCCCGGCGAT GTGGGTTGCT  10160
10161 CGTCTGGGAC CTCGGGCATG CCCATACACG CACAACAGG ACGCCCGCACC GGATGGGACG TCGTAAGGGG GCTGGGGTA  10240
10241 GCTGGGTGGG GTTTGTGCAG AGCAATCAGG GACGCCAGCC ACGCCATACA ATCGCGCTCC CGTCCGTTTG TCCGGGCAG  10320
10321 TACCACGCCG TACTGGTATT CGTACCGGCT GAGCAGGGTC GGTTGGGGGC CGCGGGAAC GGGGTCCACG CCGGAGATA  10400
10401 CCAGGTCCA CTCGGGGAAA AACCGAGTCG GCACGGCCA ACCACGCGT CTGGGGTCTT GATGCAGATA CCGGAGATA  10480
10481 AATCTTACCC CGAGCCGGAT TTTTTGGGCG TATTGAGAA ACGGCACACA CAGATCCGCC GCGCCTACCA CCCACAAGTG  10560
10561 GTAGAGGCGA GGGGGGCTGG GTTGGTCTG GTGCAGCAGT ACGGAAGCACG CAGGACCTTC CACGACGTC GTGCTCTCCA  10640
10641 AGGGGCTGTC CTCCGCAAAC AGGCCCGTGG TGTGTTTGG GGGGCAGCGA CAGGACCTAG TGCCGACGAT CGGGCGGGTG  10720
10721 GGTTGGGTA AGTCCATCAG CGGCTCGGCC AACCGTCGAA GGTTGGCCGG ACGAACGACG ACCGGGGTAC CCAGGGGTTC  10800
10801 TGATGCCAAA ATGCGGCACT GCCTAAGCAG GAAGCTCCAC AGGGCCGGC TTGCGTCGAC AGGAGTCCGG GGAAGTCCGG GCAGGGCGT  10880
```

Fig. 10E

```
10881 TGTTCTGGTC AAGGAGGGTC ATTACGTTGA CGACAACAAC GCCCATGTTG GTATATTACA GGCCCGTGTC CGATTTGGGG 10960
10961 CACTTGCGAGA TTTGTAAGGC CACGCACGCG GGGGAGACAG TTGAGCGAC GGGCTGCTCT AAAAATTTAA GGGCCCTACG 11040
11041 GTCCACAGAC CCGCCTTCCC GGGGGGCCC TTGAGCGAC CGGCAGCGGA GGCGTCCGG GAAGGGGAGG GTGATTTACG 11120
11121 GGGGGGTAGG TCAGGGGGTG GGTCGTCAAA CTGCCGCTCC TTAAAACCC GGGCCCGTC GTTCGGGGTG CTCGTGTGTT 11200
11201 GGCACTCACG GTGCGGCGAA TGGCCTGTCG TAAGTTTTGT CGGGTTTACG GGGACAGGG CAGGAGGAAG GAGGAGCCG 11280
11281 TCCCGCCCGA GACAAAGCCG TCCCGGGGTGT TTCCTCATGG CCCCTTTTAT ACCCCAGCCG AGGACGGTG CCTGGACTCC 11360
11361 CGGCCCCCGG AGACCCCCCAA ACCTTCCCAA ACCACACCAC CCAGCGAGGC CGAGCGCTG TGTCATCTGC AGGAGATCCT 11440
11441 TGCCCAGATG TACGGAAACC AGACTACCC CATAGAGGA GACCCCAGCC GGATGCCGC GGACGATGTC GACGAGGACG 11520
11521 CCCCGGACGA CGTGGCCTAT CGGAGGAAT ACGCAGAGGA GCTTTTTCTG CCCGGGACG CGACCGGTCC CCTTATCGGG 11600
11601 GCCAACGACC ACATCCCTCC CCCGTGTGC GCATCTCCCC CCGTATACG ACGACGAGC CGGGATGAGA TTGGGCCAC 11680
11681 GGGATTTACC GGGAAGAGC TGGACGCAT GGACAGGAG GGGCTCGAG CCATCAGCCG CGGCGGCAAG CCCCCCTGA 11760
11761 CGATGCCAA GCTGGTGACT GGCATGGGCT TTACGATCCA CGGAGCGCTC ACCCCAGGAT CGGAGGGGTG TGTCTTTGAC 11840
11841 AGCAGCCATC CAGATTACCC CCAACGGGTA ATCGTGAAGG CGGGGCTGGTA CACGAGCACG AGCCACGAGG CGGACTGCT 11920
11921 GAGGCGACTG GACCACCCGG CGATCCTGCC CCTCCTGAC CTGCATGTCG TCTCCGGGGT CACGTGTCTG GTCCTCCCCA 12000
12001 AGTACCAGC CGACCTGTAT ACCTATCTGA GTAGGCGCT GAACCCACTG TCTCCGGGGT GGACCCCCGC AGATGCGAGC GGTCTCCCGG 12080
12081 CAGCTCCTAA GGGCCGTTGA CTACATTCAC CGGCAGGGCA TTATCCACCG CGACATTAAG ACCGAAAATA TTTTATTAA 12160
12161 CACCCCCGAG GACATTTGCC TGGGGACTT TGGGCCCGCG AGGGTTCCCG CGACATTACCA ATCAAGCCCC TTCCCCTACG 12240
12241 GAATCGCCGG AACCATCGAC ACCAACGCCC CCGAGTCCT CCGTATACCA CGACCGTCGA CATTTGGAGC CATTTGGAGC 12320
12321 GCCGGTCTGG TGATCTTTGA GACTGCCGTC CACAACGGT GCCGCCCCGC GGCCCCAAAA GGGGCCCGTG 12400
12401 CGACAGTCAG ATCACCCCGA TCATCCGACA GGCCCAGTC CACGTTGACG AGTTTTCCCC GCATCCAGAA TCGCCCTCA 12480
12481 CCTCGCGCTA CGCTCCCCGG GGGACCCGGA ACAATCGCCC GCCTACACC CCACGGCCT GGACCCGCTA CTACAAGATG 12560
12561 GACATAGACG TGTTTGCAAA TGAATATCT GGTTTGCAAA GCCCTCACCT TGACGGCGC GCTTCGCCCC AGCGCCGCAG AGCTGCTTTG 12640
12641 TTTGCCGCTG TTTCAACAGA AATGACCGCC CCCTGGGGC GGTGCTGTTT GGGGTTGGC ACAAAAGAC CCGATCCGC 12720
12721 GTCGTGGTG TTTTTGGCAT CATGTCGCAG GGCGCCATGC GGGGGCCATGC GGGGCCATGC CCATTATC CCATTCCTTT TGTTCCTTGT 12800
12801 CGGTGTATCG GGGT                                                                                 12815
         |          |          |          |          |          |          |          |
         10         20         30         40         50         60         70         80
```

COMPOSITIONS AND METHODS FOR TREATMENT OF HERPESVIRUS INFECTIONS

This is a division of application Ser. No. 08/065,146, filed May 20, 1993 which is now abandoned.

This invention was made with U.S Government support (National Institute of Health Grant Nos. SR37CA20260-17 and 2PO1A124010-06) and the U.S. Government therefore has certain rights in the invention.

BACKGROUND OF THE INVENTION

The field of the invention is viral latency.

Herpesviruses are a family of large double stranded DNA-containing viruses many members of which are important human pathogens. A ubiquitous property of the herpesviruses is their capacity to cause both acute (productive) and latent infections in the human host, each of which is characterized by marked differences in viral transcription, DNA replication and in DNA structure.

Herpes simplex virus type 1 (HSV-1), a member of the herpesvirus family, is the causative agent of a variety of diseases in humans including, but not limited to, gingivostomatitis, genital herpes, meningoencephalitis, keratoconjunctivitis, eczema herpeticum and systemic herpes virus disease of the newborn.

Expression of HSV-1 genes during productive infection proceeds in a coordinate and sequential manner (Honess et al., 1984, J. Virol 14:8–19). The classification of HSV-1 proteins into broad sequential groups, immediate-early (IE), early (E), delayed early (DE), and late (L), is based on the kinetics of synthesis of individual viral transcripts and proteins, the effects of various metabolic inhibitors on DNA, RNA and protein synthesis, and studies using viral mutants.

The IE proteins, synthesized first in productively infected cells, are the major regulatory proteins of the virus. They are required for the synthesis of E, DE and L proteins and for the repression of their own synthesis. When virus infection occurs in the presence of inhibitors of protein synthesis such as cycloheximide, only transcripts specifying the IE proteins are synthesized (Honess et al., 1974, J. Virol. 14:8–19; Honess et al., 1975, Proc. Natl. Acad. Sci. USA 72:1276–1280).

In contrast to the complex sequence of events which occurs during productive infection, viral gene expression during latency is relatively simple. In latently infected cells, viral gene expression is limited to the latency-associated transcripts (LATs), a family of transcripts ranging in size from 2.0 to >8 kilobase pairs (kb) (Stevens et a., 1987, Science 235:1056–1059; Spivak et al., J. Virol. 61:3841–3847; Zwaagstra et al., 1990, J. Virol. 64:5019–5028). The factors which mediate the switch from productive infection to latency are not known.

Physical mapping studies have established that four of the five IE regulatory genes are located totally or in part within b a c repeat sequences flanking the unique long ($U_L$) and unique short ($U_S$) regions of the genome, whereas nearly all of the E, DE and L genes are contained within unique sequence DNA (Davison et al., 1981, J. Gen. Virol. 55:315–331; Murchie et al., 1982, J. Gen. Virol. 62:1–15; McGeoch et al., 1985, J. Mol. Biol. 181:1–13). This arrangement ensures that genes and other elements encoded totally within the repeats are diploid in all viral genomes. In addition to IE regulatory genes, the b a c repeats contain other genes and cis-acting elements which play a role in productive replication and latency. These include the sequences specifying the LATs (Stevens et al., 1987, Science 235:1056–1059; Wagner et al., 1988, J. Virol. 62:4577–4585; Krause et al., 1988, J. Virol. 62:4819–4823; Mitchell et al., 1990, J. Gen. Virol. 71:125–132; Devi-Rao et al., 1991, J. Virol. 65:2179–2190); the gene encoding a neurovirulence factor, ICP34.5 (Chou et al., 1990, Science 250:1262–1266); the a sequence which contains cis-acting elements involved in circularization, packaging and recombination of the viral genome (Smiley et al., 1992, J. Virol. 66:7505–7510); and, oriS, an origin of viral DNA replication (Weller et al., 1983, J. Virol. 45:354–366).

SUMMARY OF THE INVENTION

The invention features a substantially pure preparation of an HSV junction-spanning transcript (L/ST) characterized by the fact that the 5' end of the L/ST maps to the b repeat sequences of HSV DNA at approximately 3 kb and 125 kb, the 3' end of the L/ST extends into the c repeat sequences of HSV DNA and the HSV DNA sequence encoding the L/ST is preceded by an ICP4 binding site and a TATA box.

In one aspect, the L/ST of the invention is 2.3 kb, 4.2 kb, 7.3 kb, 8.5 kb or greater than 9.5 kb in length.

The virus encoding the L/STs of the invention is preferably HSV-1 or HSV-2.

The invention also features a substantially pure preparation of an HSV-specific nucleic acid (either DNA or RNA) which encodes the L/ST of the invention, and further features a vector comprising this nucleic acid and a cell comprising this vector. The cell comprising the vector may also express the nucleic acid encoding the L/ST.

Another feature of the invention is a substantially pure preparation of a polypeptide, or a fragment thereof, encoded by the L/ST of the invention.

The invention also features an antibody which binds preferentially to a polypeptide encoded by the L/ST of the invention.

Also featured in the invention is a method of identifying a compound capable of inhibiting the synthesis of an L/ST. The method involves infecting cells in culture with an ICP4-minus HSV, administering the compound to the cells either prior to or following infection with the ICP4-minus HSV, and monitoring the cells for the presence or absence of the L/ST. The absence of the L/ST is an indication that the compound inhibits the synthesis of the L/ST and the presence of the L/ST is an indication that the L/ST does not inhibit the synthesis of the L/ST.

A further feature of the invention is a method of treating a human patient infected with HSV by administering to the patient a compound capable of inhibiting the synthesis of an L/ST in a pharmaceutically acceptable composition.

Compositions and methods designed to inhibit establishment of or reactivation from latency are crucial to treatment of infections caused by HSV, because of the central role which the latent state plays in the pathogenicity of this virus.

By L/ST is meant an HSV-specific junction-spanning transcript which is characterized as follows: (i) the 5' end of the transcript maps to the b repeat sequence of HSV DNA at or about 3 kb and at or about 125 kb within the 152 kb viral genome; (ii) the transcript extends into the c repeat sequences; and, (iii) the DNA sequence encoding the 5' end of the transcript is preceded by an ICP4 binding site and a TATA box.

By junction-spanning transcript is meant a transcript whose sequence spans the junction between the long and short region of the HSV genome.

While the transcript was initially discovered in cells infected with an ICP4-minus mutant of HSV-1, any transcript which is at least 50% homologous, preferably 60% homologous, more preferably 80% homologous and most preferably 90% homologous to an L/ST expressed in ICP4 mutant-infected cells, is also included in the invention. Furthermore, the invention includes L/STs as defined above which are encoded by HSV-2.

The present invention also provides for analogs of proteins or peptides encoded by L/STs. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for biologically active fragments of the polypeptides. An L/ST-specific polypeptide is biologically active if it inhibits the synthesis or function of the naturally encoded protein or polypeptide encoded by L/STs in the assays described below.

As used herein, the term fragment, as applied to a polypeptide, will ordinarily be at least about five contiguous amino acids, typically at least about ten contiguous amino acids, more typically at least about twenty continuous amino acids, usually at least about thirty contiguous amino acids, preferably at least about forty continuous amino acids, more preferably at least about fifty contiguous amino acids, and most preferably at least about sixty to eighty or more contiguous amino acids in length.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

DETAILED DESCRIPTION

The Drawings are first described.

The Drawings FIG. 1 is a physical map of the internal repeat region of HSV-1 DNA.

A) A diagram of the HSV-1 genome. $U_L$=unique long segment; $U_S$=unique short segment; b=inverted repeat sequence bracketing $U_L$; c=inverted repeat sequence bracketing $U_S$; a=a 317 bp sequence between the b and c sequences.

B) An expanded map of internal repeat sequences lying between map units 117–134.5 kb on the physical map of the HSV-1 genome (Davison et al., 1981, J. Gen. Virol. 55:315–331; Murchie et al., 1982, J. Gen. Virol. 62: 1–15; McGeoch et al., 1985, J. Mol. Biol. 181:1–13). Beneath the scale of kilobase pairs are shown the locations of the b, a and c sequences and relevant restriction sites in KOS DNA. Beneath the map of restriction sites are shown the locations of the genes and cis-acting elements contained within sequences 118–134 kb. Specifically, the map shows the locations of sequences specifying the small (1.5 and 2.0) kb and large (8.3 and putative 6 kb) LATs, the transcripts encoding ICP0, ICP34.5, ICP4, and ICP22, oriS, and the transcripts designated oriS RNA1, and oriS RNA2. Open reading frames are shown as hatched bars.

(C) DNA sequences specifying the riboprobes (arrows) used in this study. The arrows represent the orientation of these sequences in the pGEM vector as driven by the SP6 promoter. The shaded area in FIG. 1B, C, D and E, indicates the region of the HSV-1 genome from which transcripts synthesized from left to right would be detected using these riboprobes.

(D) Sequence specifying the DNA probe (bar) used for S1 nuclease mapping. The probe was labelled at the BssHII site (asterisk).

(E) Locations of the mutations in the four mutant viruses used in these studies. n212 and n12 contain nonsense mutations in the ICP0 and ICP4 genes, respectively. The open boxes indicate the sequences deleted in dlLAT1.8 which specifies no detectable LATs, and d120, an ICP4 null mutant.

FIG. 2 is an autoradiogram depicting the results of Northern blot analysis of total RNA from KOS- and mutant virus-infected cells.

(A) NB41A3 cells were mock-infected or infected with KOS or mutant viruses n12 and d120 (ICP4), n212 (ICP0), 22n199 (ICP22), 5dl1.2 (ICP27), and dlLAT1.2 (LATs) at a multiplicity of 10 PFU/cell. Total RNA was isolated at 18 hours post-infection (pi), separated electrophoretically and transferred to Magnagraph paper. The viral transcripts were detected by Northern blot analysis using a riboprobe derived from pEBN9-LAT (FIG. 1C). The locations of RNA size markers are indicated on the right. The approximate sizes of the transcripts detected are indicated on the left.

(B) NB41A3 and E5 cells were mock-infected or infected with KOS or n12 at a multiplicity of 10 PFU/cell. Total RNA was analyzed by Northern blot hybridization as described above.

Figure 3:
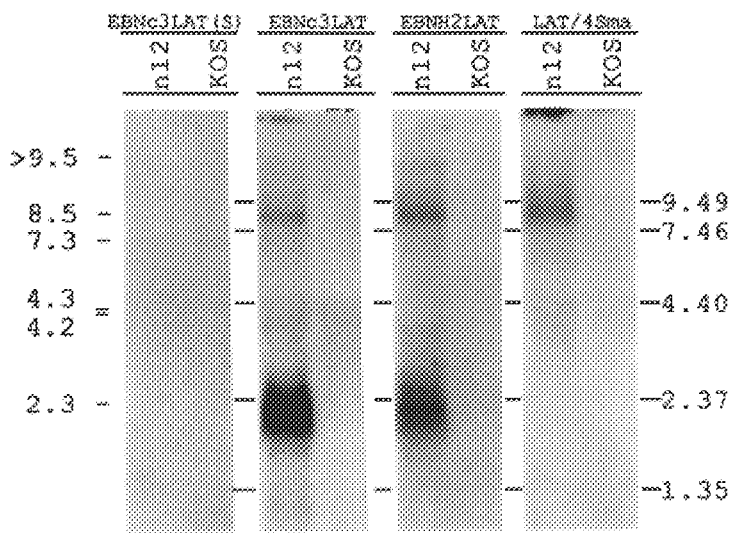

FIG. 3 is an autoradiogram depicting physical mapping of viral transcripts present in total cell RNA from KOS- and n12-infected NB41A3 cells by Northern blot analysis. NB41A3 cells were mock-infected or infected with KOS or n12 at 10 PFU/cell. At 18 hours pi, total RNA was harvested, separated and transferred to Magnagraph paper. The RNA blot was divided into four strips each of which was probed with the riboprobe listed above each lane. No signal was detected in mock-infected cells using any of the probes. RNA size markers are shown on the right and the sizes of the transcripts which were detected are indicated on the left.

Figure 4:
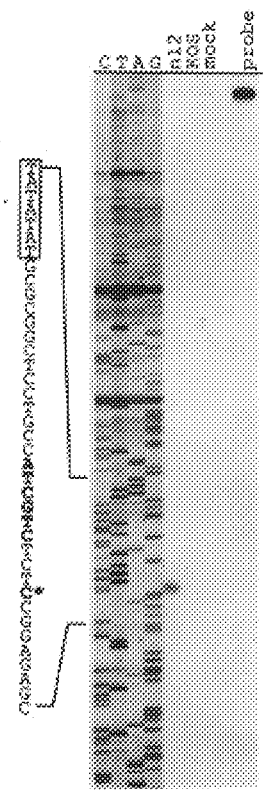

FIG. 4 is an autoradiogram depicting S1 nuclease analysis of the 5' end of the L/STs. RNA obtained from NB41A3 cells mock-infected with either KOS or n12 was harvested at 18 hours pi. 5 µg of RNA was hybridized to the StuI-BssHII probe (FIG. 1D) and was subsequently digested with 1000 units of S1 nuclease. DNA sequencing was performed by the Sanger method (Sanger et al., 1977, Proc. Natl. Acad. Sci. USA 74:5463–5476). The nucleotide to which the band in the lane labelled n12 corresponds is the C indicated by the asterisk. The sequence upstream of the transcriptional start site including a TATA box and a consensus ICP4 binding site (ATCGTC) is shown on the left.

Figure 5:
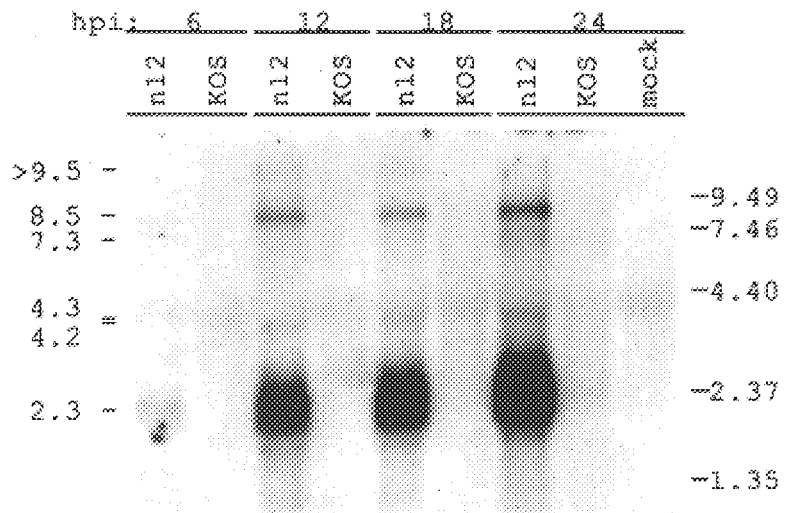

FIG. 5 is an autoradiogram depicting the kinetics of expression of the L/STs in NB41A3 cells. RNA from NB41A3 cells infected with 10 PFU/cell of KOS or n12 was harvested at 6 hour intervals through 24 hours pi. Mock-infected cells were harvested at 24 hours pi. RNA was analyzed by Northern blot hybridization using a riboprobe derived from pEBN9-LAT (FIG. 1C). The sizes of the four L/STs are indicated on the left. RNA size markers are shown on the right.

Figure 6:
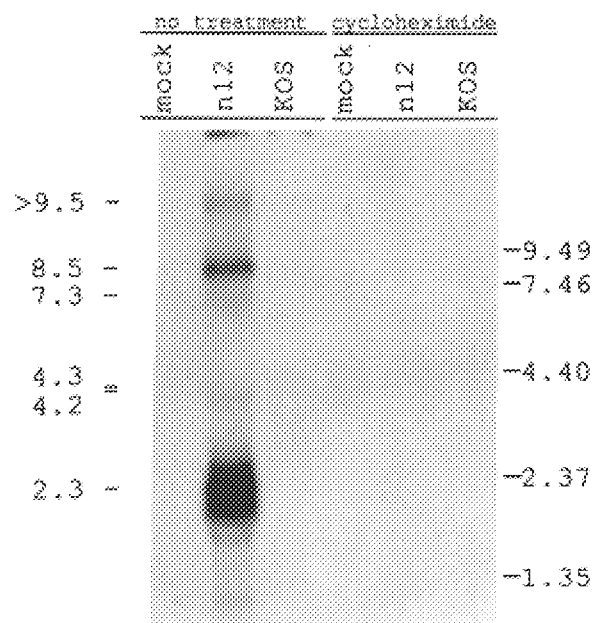

FIG. 6 is an autoradiogram depicting the effect of cycloheximide on expression of the L/STs. NB41A3 cells were treated with 50 µg/ml cycloheximide for 1 hour prior to mock-infection or infection with 10 PFU/cell of KOS or n12. Untreated cells were included as a control. RNA was harvested at 12 hours pi and analyzed by Northern blot hybridization using a riboprobe derived from pEBN9-LAT (FIG. 1C). The sizes of the L/STs are indicated on the left. RNA size markers are shown on the right.

Figure 7:
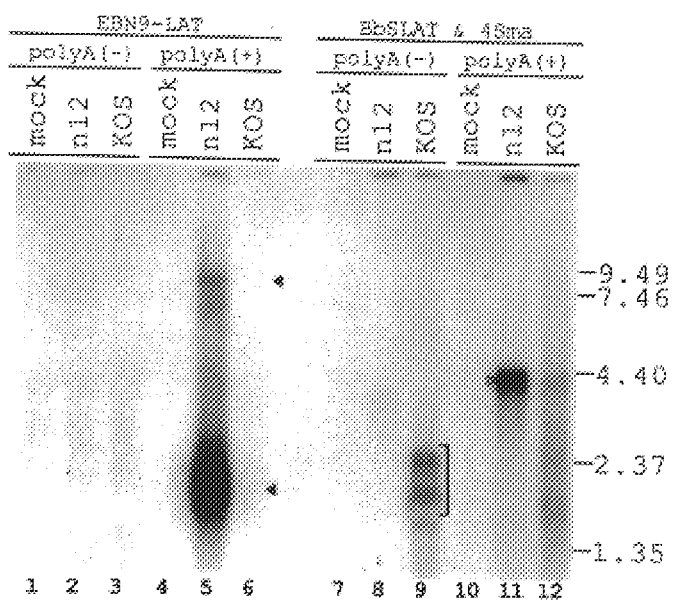

FIG. 7 is an autoradiogram depicting polyadenylation of the L/STs. RNA obtained from mock-infected or KOS-infected NB41A3 cells (at a multiplicity of 10 PFU/cell) was harvested at 24 hours pi. RNA (120 µg) was separated into poly A(+) and poly A(-) fractions using the Promega PolyATract™ mRNA isolation system. 15 µg of Poly A(-) RNA and one-fourth of the total yield of poly A(+) RNA was loaded into each lane of the gel. Following electrophoresis and transfer, lanes 1–6 were probed with pEBN9-LAT (FIG. 1C) in order to detect the L/STs. Lanes 7–12 were probed with pBbSLAT and p4Sma (FIG. 1C) in order to detect transcripts specifying the LATs and ICP4. L/STs are indicated by filled arrowheads. The LATs are indicated by the bracket. ICP4-specific mRNA is indicated by the hollow arrowhead.

FIG. 8 is an expanded physical map of the region of HSV-1 DNA encoding the L/STs.

A) Beneath the scale of kb are the locations of the b, a and c sequences and of relevant restriction sites in KOS DNA. Beneath the map of restriction sites are the coding sequences for the ICP0 (partial), ICP34.5, ICP4, oriS RNAs 1 and 2, and ICP22 transcripts. OriS is is located between the 5' start sites of the ICP4 and ICP22 transcripts.

B) Location of sequences specifying L/STs. The direction of transcription is indicated by the arrows. The 5' end of the transcripts lies between the NotI and SacI sites shown in FIG. 1A and D. The 3' ends of the transcripts have not been mapped and are shown in parentheses.

C) The locations of the four potential open reading frames encoded within the abundant 2.3 kb L/ST are shown as open boxes beneath the >9.5 kb transcript.

D) Nucleotide sequence of HSV-1 DNA between StuI and BssHII sites. The E4TF1 recognition site (Jones et al., 1988, Genes and Dev. 2:267–281) and the ICP4 binding site ATCGTC are shown as closed boxes beneath the lines. The TATA box is also shown as a closed box. The sequence specifying the N-terminus of the 234 aa open reading frame is shaded. The transcriptional start site is indicated by an arrow.

FIGS. 9 A–D depicts the HSV-1 L/ST nucleotide and corresponding amino acid sequence specifying (A) ORF-1; (B) ORF-2; (C) ORF-3; and (D) ORF-4.

FIG. 10 (covering 5 pages) depicts the nucleozide sequence of HSV-1 DNA in the region of the HSV-1 genome encoding the L/STs. The TATA box and the ICP4 binding site are underlined and are indicated to the right on the first page of the figure. The 5' end of the L/STs (nucleotide 125,042 on the HSV-1 genome is indicated by a dot over the base C, which is also underlined. The first codon (ATG) of ORF-1 is underlined as is the poly A site of the 2.3 kb L/STs.

The present invention provides novel compositions and methods for the treatment of herpes simplex viral infections. The examples given below relate to, but are not limited to treatment of HSV-1 infections. These treatments are also applicable to the treatment of herpes simplex virus type 2 (HSV-2) infections because of the extensive sequence homology between these two viruses.

The data presented below demonstrate the discovery of a new class of HSV-1-specific transcripts which span the L/S junction. They have therefore been designated L/S junction-spanning transcripts or L/STs. These transcripts were first identified in cells infected with an ICP4 null mutant. The experiments reported herein establish the potential importance of these transcripts in the establishment of latency by HSV, or in reactivation of this virus from the latent state.

Materials and Methods

Cells and Viruses. African green monkey kidney cells (Vero, ATCC CCL 81), E5 cells (Vero cells stably transformed with the wild-type gene for ICP4; DeLuca et al., 1985, J. Virol. 56:558–570), 0–28 cells (Vero cells stably transformed with the wild-type gene for ICP0; Sacks et al., 1987, J. Virol. 61:829–839), and 3—3 cells (Vero cells stably transformed with the wild-type gene for ICP27; McCarthy et al., 1989, J. Virol. 63:18–27), were grown and maintained in Dulbecco's modified Eagle medium (DME, Gibco Laboratories, Inc., Gaithersburg, Md.) as described (Sacks et al., 1985, J. Virol. 55:796–805). Mouse neuroblastoma cells (NB41A3, ATCC CCL147) were propagated in F10 medium (Gibco Laboratories, Inc.) supplemented with 2.5% fetal calf serum, 15% horse serum, 100 units/ml penicillin and 100 μg/ml streptomycin. Rat pheochromocytoma cells (PC12) were propagated and maintained as described (Greene et al., 1982, Adv. Cell Neurobiol. 3:373–414).

In the experiments described below, the KOS wild-type strain of HSV-1 (Schaffer et al., 1978, Virol. 27:490–504) and seven mutants derived from KOS were used. The ICP4 nonsense and deletion mutants, n12 and d120, respectively, were grown and assayed on E5 cells (DeLuca et al., 1985, J. Virol. 56:558–570; DeLuca et al., 1988, J. Virol. 62:732–743). Mutant n12 contains a nonsense insertion at codon 12 in the ICP4 coding sequence, and d120 lacks coding sequence for all but the first N-terminal amino acids of ICP4. Neither virus expresses detectable ICP4 transregulatory activity so both are null mutants. The ICP0 nonsense mutant, n212, was grown in Vero cells and assayed on 0–28 cells (Cai et al., 1989, J. Virol. 63:4579–4589). The ICP27 deletion mutant, 5dl1.2, was grown and assayed in 3—3 cells (McCarthy et al., 1989, J. Virol. 63:18–27). KOS, an ICP22 nonsense mutant named 22n199, and the LAT deletion mutant, dlLAT1.8 (Leib et al., 1989, J. Virol. 63:2893–2900), were grown and assayed on Vero cells. Like n12 and d120, the other mutants n212, 5dl1.2, 22/n199 and dlLAT1.8 are also null mutants in that they fail to express their respective products.

Riboprobes. The BamHI K fragment containing the b a c repeats from the plasmid pSG28 (Goldin et al., 1981, J. Virol. 38:50–58) was cloned into the expression vector pGEM3Zf(+) to yield pBamK (Promega, Madison, Wis.) (FIG. 1C). The 1,750 bp NcoI fragment from pBamK (map units 124–125.8) was subcloned into pGEM3Zf(+). This fragment was cleaved with StuI and the resulting fragments were cloned into pGEM3Zf(+) to yield pEBNc3-LAT(s) (NcoI-StuI) and pEBNc3-LAT (StuI-NcoI). Plasmid pEBN9-LAT contains the NotI subfragment of HSV DNA from pEBNc3-LAT. Plasmid pEBNH2-LAT contains the NotI-HincII fragment from pBamK, and pLAT/4Sma contains the SmaI fragment from plasmid pn11 (DeLuca et al., 1987, Nucl. Acids Res. 15:4491–4511), which contains the wild-type ICP4 gene. Riboprobes capable of detecting transcripts in the sense orientation of LAT were prepared from these plasmids according to the manufacturer's instructions (Promega).

Northern blot analysis. Approximately $4 \times 10^6$ cells were seeded in 100 mm petri dishes 24 hours prior to infection. Cells were infected at a multiplicity of 10 PFU/cell in 0.5 ml of medium. After absorption for 1 hour at 37° C., medium was added to infected cells and incubation was continued at 37° C. for the indicated times post-infection (pi). To harvest RNA, monolayers of cells were first washed twice with cold phosphate buffered saline (PBS) and scraped into 0.5 ml GIT buffer (4M guanidine isothiocyanate, 25 mM sodium acetate, 100 mM β-mercaptoethanol). The volume was adjusted to 3.0 ml with GIT buffer and the cell suspension was subjected to Vortex mixing for 15 seconds to shear the DNA. The GIT/RNA solution was loaded onto a 2 ml cesium chloride cushion (5.7M cesium chloride, 25 mM sodium acetate) and the sample was centrifuged at 35,000 rpm in a SW50.1 or SWi55.1 rotor at 20° C. for 18 hours. The RNA pellet was resuspended in diethyl pyrocarbonate(DEPC)-treated water and ethanol precipitated once prior to resuspension in 100 μl DEPC-water followed by spectrophotometric quantitation.

Fifteen μg of RNA obtained as just described was heat denatured (15 minutes, 68° C.), applied to an agarose gel [1% agarose, 16.6% formaldehyde, 1×MOPS (20 mM 3-N-[Morpholinol] propane-sulfonic acid, 1 mM sodium acetate, 1 mM EDTA)], and electrophoresed overnight at 35V in 1× MOPS buffer. The gel was washed once in water and four times in 10× SSC (1.5M sodium chloride, 0.15M sodium citrate, pH 7.0) (15 minutes per wash) before transfer to a Magnagraph nylon membrane (Micron Separations, Inc., Westboro, Mass.) in 10× SSC. The blot was baked at 85° C. under vacuum for 2 hours. The blot was prehybridized overnight at 68° C. in 50% formamide, 5× Denhardt's solution [5 mg/ml Ficoll (Type 400; Pharmacia, Piscataway, N.J.), 5 mg/ml polyvinylpyrrolidone, and 5 mg/ml bovine serum albumin (Fraction 5; Sigma, St. Louis, Mo.)], 6× SSPE (0.9M sodium chloride, 60 mM sodium phosphate monobasic, 6 mM EDTA, pH 7.5), 0.2% SDS, and 100 μg/ml salmon testes DNA. Riboprobes were added to the blot in prehybridization buffer for incubation overnight at 68° C. The blot was rinsed once briefly in 2× SSC/1% SDS, washed for two 15 minute periods in 2× SSC/1% SDS at room temperature, twice for 15 minutes in 0.1× SSC/0.1% SDS at 68° C., and once for 15 minutes in 0.1× SSC/0.1% SDS at 85° C. Bands were visualized by autoradiography.

S1 Nuclease Analysis. The S1 nuclease mapping procedure used in these studies has been described in Imbalzano et al. (1990, J. Virol. 64:2620–2631). To map the 5' end of the L/STs, plasmid pEBNc3-LAT (FIG. 1C) was digested with BssHII, end-labeled with $^{32}$p, and digested with StuI to yield a 443 bp double-stranded DNA probe (FIG. 1D). The probe and 5 μg total RNA were denatured at 85° C., hybridized at 65° C. overnight, and digested with 1000 units of S1 nuclease (Gibco) at 40° C. for 40 minutes. Sequencing was performed by the Sanger method (Sanger et al., supra) using the Sequenase Version 2.0 reagents of United States Biochemical (Cleveland, Ohio). The primer sequence was 5'-CGCGCCGCGGCTCGTGGG-3', of which the 5' terminal nucleotide corresponds to the labeled nucleotide of the S1 probe.

Isolation of mRNA. Polyadenylated mRNA and non-polyadenylated RNA was separated from total cell RNA using the PolyATract™ mRNA isolation system purchased from Promega. Total cell RNA was isolated as described above from NB41A3 cells infected with 10 PFU/cell of either n12- or KOS was harvested at 24 h PI.

Results

Viral transcripts specified by the b sequences are synthesized in cells infected with ICP4 null mutant viruses. In order to fine-map LAT transcripts expressed from the b a c repeat sequences in cells of neural origin, Northern blot analysis of RNA obtained from NB41A3 cells infected with wild-type strain KOS or KOS mutants was performed. ICP4 null mutants n12 and d120 (FIG. 1E) were used in these experiments because it was likely that in the absence of ICP4, the levels of detectable LATs would be increased, since ICP4 has been shown in transient assays to suppress LAT expression (Batchelor et al., 1990. J. Virol. 64:3269–3279). Unexpectedly, a new class of viral transcripts heretofore unknown, was discovered.

Figure 2A:
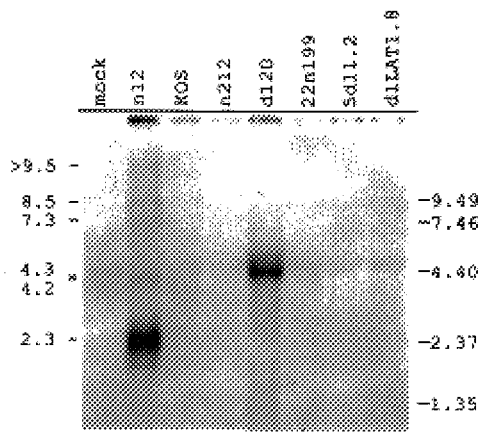

As shown in FIG. 2A, when a riboprobe derived from pEBN9-LAT was used as a hybridization probe, abundant transcripts of 2.3 kb and less abundant transcripts of 4.2, 7.3, 8.5, and >9.5 kb were detected in n12-infected cells but not in cells infected with KOS, n212, 5dl1.2, 22/n199 or dlLAT1.8 . In cells infected with the ICP4 deletion mutant, d120, a single abundant 4.3 kb transcript was detected. Based on the size of the deletion in d120 (4.1 kb), the 4.3 kb species in d120-infected cells may be a stable but deleted form of the larger 8.5 kb species. Upon close inspection, the 2.3 kb species synthesized in n12-infected cells appears to consist of four or more transcripts differing in size by a uniform unit length.

The results of Northern blot analysis demonstrated that a series of transcripts encoded in part by sequences in the b repeat was expressed at high levels in the absence of ICP4, but not in KOS-infected cells or in cells infected with mutants defective in ICP0, ICP22, ICP27 or the LATs. Identical results were obtained in Vero, HEL, and PC12 cells.

Figure 2B:
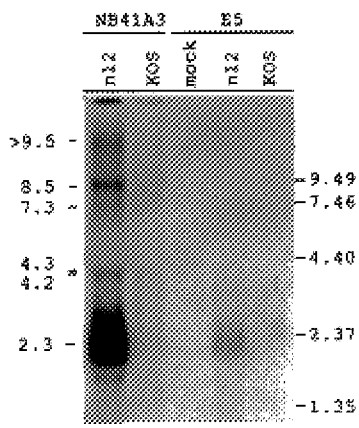

Further evidence that expression of the novel transcripts is repressed in the presence of ICP4 was obtained by infecting ICP4-expressing E5 cells with n12 and KOS (FIG. 2B). In these tests, low levels of the 2.3 kb transcript were detected in n12-infected but not in KOS-infected E5 cells. Because E5 cells express ICP4 at levels that are insufficient to fully complement ICP4 null mutants (DeLuca et al., 1985, Mol. Cell. Biol. 5:629–637), synthesis of the novel transcripts was not fully suppressed.

Mapping the transcripts. A series of contiguous sense-specific riboprobes were used to better define the 5' and 3' ends of the novel transcripts in n12-infected cells. RNA from KOS-infected cells was used as the negative control. When infected NB41A3 cell RNA was harvested at 18 hours pi and examined by Northern blot analysis, two abundant (2.3 and 8.5 kb) and three less abundant transcripts (4.2, 7.3 and >9.5 kb) synthesized in the same orientation (sense) as the LATs were detected in n12- but not in KOS-infected cells (FIG. 3). In three independent tests, the abundant 2.3 kb transcript was detected using probes EBNc3-LAT and EBNH2-LAT; however, probes capable of detecting upstream and downstream sequences [EBNc3-LATS and LAT/4Sma, respectively] did not detect this transcript. A shortened version of the EBNH2-LAT probe extending from the XcmI to the HincII site (FIG. 1C), also failed to detect the small transcript, indicating that the 3' terminus of the 2.3 kb species is near the XcmI site. The larger, less abundant 8.5 kb transcript was detected with probes EBNc3-LAT, EBNH2-LAT, and LAT/4Sma but not with EBNc3-LATS (FIG. 3). The absence of detectable hybridization with EBNc3-LATS suggests that the 2.3 and the 8.5 kb transcripts are 5' coterminal and that the terminus of the transcripts is near the StuI site (FIG. 1B). The 8.5 kb transcript was also detected with riboprobes 22SS and 22KS (FIG. 1C), which at very early times pi would hybridize to the ICP22 transcript at the amino and carboxyl half, respectively, of the ICP22 open reading frame.

The 2.3 and 8.5 kb transcripts thus appear to share a 5' start site which is positioned within the b repeats near the StuI site (FIG. 1B). Both transcripts span the L/S junction and the 2.3 kb transcript likely terminates in the c repeats near the XcmI site. Based on its estimated size and assuming a start site near the StuI site in the b repeats, the 8.5 kb transcript probably terminates near the SphI site in the ICP22 coding sequences in $U_s$ (FIG. 1B). Because these novel transcripts span the junction between the long (L) and short (S) region of the genome, they have been designated L/S junction-spanning transcripts or L/STs.

Mapping the 5' end of the L/STs. In order to better define the 5' start site of the L/STs, S1 nuclease mapping was performed. The probe used in these tests was the 443 bp StuI-BssHII fragment, labelled at the BssHII end (FIG. 1D). As shown in FIG. 4, the 5' terminus of the L/STs maps to a C residue 28 bp downstream of a TATA box and 6 bp downstream of an ICP4 consensus binding site (ATCGTC).

Mapping of the 3' end of the L/STs. The 3' end of each of the L/STs can be mapped in a manner similar to that described above for the 5' end. The sequence of the entire HSV-1 genome is known (GenBank HE1CG, Accession No. x14112 D00317 D00374) and the sequence of the region of HSV-1 DNA encoding the L/STs is shown in FIG. 10. A search of the DNA sequence corresponding to the 2.3 kb L/STs reveals a marked absence of splice signals, suggesting that the DNA encoding these L/STs is unlikely to contain introns. Therefore, in order to map the 3' ends of each of these transcripts, probes can be obtained which correspond to regions of DNA predicted to encompass each of the 3' termini. These probes can be hybridized to the appropriate RNA which is then subjected to S1 nuclease analysis as described above.

Similar experiments can be conducted in order to map the 3' ends of the remaining L/STs. First, the DNA sequence encoding these transcripts can be examined for the presence of splice signals. The putative 3' ends can subsequently be identified and probes corresponding to these 3' ends can be used in S1 nuclease assays to precisely locate these 3' ends.

The L/STs are expressed with late kinetics in ICP4 null mutant virus-infected cells. To examine the kinetics of L/ST expression, a time course experiment was performed in n12-infected NB41A3 cells (FIG. 5). Total RNA was harvested at 6 hour intervals through 24 hours pi and Northern blots were probed with a riboprobe derived from pEBN9-LAT. The 2.3 and 8.5 kb L/STs were first evident at 6 hours pi and accumulated with time through 24 hours pi. In these tests, the 4.2 and 7.3 kb species were clearly detectable at 24 hours pi. No transcripts were detected in RNA preparations from KOS-infected cells at 6, 12 or 18 hours pi, but a broad, faint band corresponding to 2.3 kb species was detected at 24 hours pi. The accumulation of the 8.5 kb (and to a lesser extent the 4.2 kb) transcripts in parallel with the 2.3 kb species, likely reflects a common promoter for these species.

L/ST synthesis requires denovo protein synthesis. In order to determine whether the L/STs are made in the presence of inhibitors of protein synthesis, Northern blot analysis was performed using total cell RNA from KOS- and n12-infected NB41A3 cells incubated in the presence of 50 µg/ml cycloheximide (FIG. 6). KOS infected cell extract was tested by Western blot analysis for the presence of ICP4 to confirm the effectiveness of the cycloheximide treatment. None was detected in treated cells whereas a single major band was detected in untreated cells. No L/STs were detected in RNA from n12-infected cells treated with cycloheximide. As in other tests the L/STs were not detected in RNA from cells infected with KOS. In the same experiment, RNA from both KOS- and n12-infected cells, treated and untreated, contained ICP0-specific RNA. Together, these findings indicate that expression of the L/STs is not dependent upon viral DNA synthesis, but that their expression is dependent upon the synthesis of other viral and/or cellular proteins whose synthesis is inhibited by cycloheximide.

The L/STs are polyadenylated. To determine whether the L/STs are polyadenylated, total cell RNA was separated into polyadenylated and non-polyadenylated fractions. The RNAs so isolated were examined by Northern blot analysis using a riboprobe derived from pEBN9-LAT (FIG. 1C). As shown in FIG. 7, the L/STs were detected in lane 5 which contained the polyadenylated fraction. A duplicate blot was used to detect an ICP4-specific transcript (lanes 11 and 12) and the LATs (lane 9) as controls for poly A(+) and poly A(−) RNAs, respectively.

Sequence homology between HSV-1 L/STs and a corresponding region in HSV-2. While the data presented above concern the identification and characterization of HSV-1-specific L/STs, the invention should not be construed to be limited to HSV-1. It is well known in the art that HSV-1 and HSV-2 share extensive sequence homology with each other. It is also well known that each of the known functions in HSV-1 has a functionally similar and often structurally (i.e., either DNA or amino acid sequence) similar counterpart in HSV-2 (Esparza et al., 1976, Virology 70:372–384). For this reason, the invention should not be construed as being solely limited to HSV-1-specific L/STs. Rather, the invention encompasses L/STs encoded by other viruses and in particular, includes L/STs encoded by HSV-2.

For example, when the DNA sequence of HSV-1 and HSV-2 in the region of the L/STs was compared, significant homology was evident. The HSV-2 genome, in a region of DNA comparable to the HSV-1 L/STs, contains a TATA box and an ICP4 binding site (McGeoch et al., 1990, J. Gen. Virol. 72:3057–3075). When the genomes of each of the two viruses were aligned beginning at the L/ST TATA box and ATCGTC ICP4 binding region through to the ICP34.5 TATA box, a 711 bp identity (71%) was found. If the a sequences were included in the analysis then an 878 bp region of identity (70%) was found.

In HSV-1, four intron-less ORFs are present within the sequence specifying the 2.3 kb L/ST. The first, ORF-1, is 234 aa in length; ORF-2 is 29 aa in length; and, ORF-3 and ORF-4 are 10 and 15 aa in length, respectively. In the corresponding region of HSV-2 there are 5 ORFs. ORF-1 is 131 aa in length; ORF-2 is 262 aa in length; ORF-3 is 28 aa in length; and, ORF-4 and ORF-5 are 4 and 143 aa in length, respectively. The HSV-1 ORF-1 corresponds to the HSV-2 ORF-1 and 48 aa of the N-terminal of each are homologous to each other. The homology between HSV-1 and HSV-2 in the region of the L/STs is therefore significant.

Identification and characterization of HSV-2 L/STs. L/STs encoded by the HSV-2 genome can be identified essentially as described above for HSV-1. Neuronal cells can be infected with an ICP4-minus HSV-2 virus and L/STs can be identified using probes which specifically hybridized to RNA sequences encoded by the L/ST region of HSV-2 DNA. Characterization of HSV-2 L/STs may be performed as described above for HSV-1 L/STs. Thus, while the examples given below refer to HSV-1, in each instance, they are also applicable to HSV-2.

Cloning and expression of the gene(s) encoding the L/STs. In order to generate large quantities of L/STs and the products they encode, the genes encoding the L/STs must first be cloned and then expressed in an expression system. The genes encoding the L/STs and their protein products may prove to be useful as therapeutic treatments for infections caused by HSV.

Sequences comprising the full length gene for the L/STs, or any subset thereof, may be cloned by any number of different procedures available in the art which are described, for example, in Sambrook et al. (1989, Molecular Cloning, A Laboratory Manual, Cold Spring Harbor, N.Y.). Essentially, a fragment of DNA comprising the desired sequence is inserted into a suitable vector using ordinary molecular biology techniques. Suitable vectors include those designed to yield large quantities of DNA encoding an L/ST, or expression vectors designed to produce large quantities of either an L/ST specific RNA or a protein encoded by an L/ST. Such vectors are available commercially and the techniques involved in cloning and/or expression of either DNA, RNA or protein are familiar to any ordinary molecular biologist. For example, the sequence encoding the desired L/ST can be cloned under the expression of either a eukaryotic or a prokaryotic promoter that is capable of driving high levels of expression of the RNA or protein products in either eukaryotic or prokaryotic cells. Alternatively, the sequences encoding an L/ST can be expressed in vitro by cloning the sequences into, for example, a pGEM vector (Promega), wherein RNA can be transcribed from such a vector in vitro by adding the appropriate prokaryotic RNA polymerase and reagents and buffers. Relatively large quantities of protein can be obtained by translation of this RNA in vitro in a rabbit reticulocyte or wheat germ system. Such technology is well known to any ordinary molecular biologist and is described in many manuals of molecular biology including Sambrook et al. (supra).

Fragments of peptides or proteins can also be obtained in relatively large quantities by cloning fragments of the respective DNA into the expression plasmids described above. Expression of such sequences in these expression systems will result in the production of fragments of proteins.

Because the sequence of the entire L/STs region is known, oligonucleotides encoding small fragments of L/STs can readily be obtained using an oligonucleotide synthesizer.

Preparation of antibodies to proteins, peptides or fragments thereof encoded by a L/ST. Antibodies directed against proteins, peptides or fragments thereof encoded by an L/ST may be useful in diagnosing latent infection by HSV and as therapeutic compositions for treatment of HSV infections.

Proteins or peptides encoded by a L/ST, or fragments thereof, obtained as described above, can be purified by electrophoresis or any ocher common protein purification technique. Polyclonal antibodies directed against such purified products can be generated using standard technology available in the art described for example, in Harlow et al. (1988, In: Antibodies, A Laboratory Manual, Cold Spring Harbor, N.Y.). Monoclonal antibodies can also be generated to proteins, peptides or fragments thereof, using standard hybridoma technology available in the art.

If the proteins or peptides can be obtained in relatively abundant quantities, polyclonal antibodies can be generated following the protocol of Jones et al. (1987, Cell 48:79), wherein the protein (approximately 200 μg) is first injected into rabbit lymph nodes followed by subcutaneous booster inoculations at regular intervals. Both preimmune serum and serum obtained after each booster can be assayed for activity against the appropriate protein or peptide using any one of several methods known to those skilled in the art, such as immunprecipitation, an enzyme-linked immunosorbent assay (ELISA), radioimmunoassay (RIA), or even an Ouchterlony double diffusion assay.

Generation of mutant viruses which are defective in the synthesis of L/STs. In order to determine the function of the L/STs, mutant viruses can be generated which are unable to express L/STs. Such mutant viruses may also be useful as vaccine candidates for the treatment and/or the prevention of HSV infections.

Mutant viruses may be generated which are defective in the synthesis of the L/STs using technology which is known in the art to generate mutations in viral genes. Because the region of DNA encoding the L/STs also encodes other HSV-1 genes, care must be taken to engineer the mutations in such a way so as to avoid creating double or even triple mutations in that region. Because of the various locations of the overlapping genes in this region, it is preferable to generate mutations in the region of DNA involved in regulating expression of the L/STs, rather than in the region of DNA encoding the L/STs. Site directed mutations in the TATA box or any other transcriptional control region should abolish the transcriptional machinery and inhibit expression of the L/STs without significantly affecting expression of other viral genes encoded by this region of DNA.

The mutations may be generated in two steps. First, specific nucleotides are altered in a plasmid comprising the promoter sequences to be mutated using oligonucleotide site-directed mutagenesis. Second, the mutated sequences within the plasmid are incorporated into the viral genome via the process of homologous recombination. One example of how this can be accomplished is described below. However, any ordinary means familiar to those in the art for introduction of mutations into viral genes, described for example in Guide to Molecular Cloning Techniques (In: Methods in Enzymol., 1987, Vol. 152, Eds. Berger and Kimmel, Acad. Press San Diego), and in Deluca et al. (1985, J. Virol. 56:558–570) may also be used provided that such mutations do not disrupt other essential viral genes.

A) Mutation of the plasmid pEBNc3-LAT to yield pLST-4H. This may be accomplished in two steps. First, two nucleotide changes are introduced such that a new restriction site (HindIII: AAGCTT), which is contiguous with the TATA box and therefore will affect the TATA box, is generated. The HindIII site is preferably placed at −32 bp relative to the 5' end of the L/STs. To accomplish this, the phagemid/plasmid pEBNc3-LAT, which contains the entire L/ST promoter through nucleotide +815 of L/ST, is transformed into *E. coli* strain CJ236. Plasmids which are propagated in this strain of *E. coli* are converted to uracil-containing plasmids. By infecting *E. coli* which contains pEBNc3-LAT with the phage, R408, single-stranded pEBNc3-LAT can be isolated. An oligonucleotide containing the desired two point mutations is then annealed to single-stranded pEBNc3-LAT and a second complementary strand is synthesized therefrom using T4 DNA polymerase and T4 DNA ligase. The product of this reaction is then transformed into *E. coli* strain HB101, which strain expresses active uracil-N-glycosylase. Thus, only the mutated, non-uracil-containing strand is capable of replication in this strain of *E. coli*, resulting in production of large quantities of a double-stranded plasmid encoding the desired mutation, termed pLST-2H.

Next, two additional T to G changes at nucleotides −25 and −26 are introduced into pLST-2H using the polymerase chain reaction (PCR). The first primer (nucleotides −44 to −9 relative to the L/ST start site) contains the two point mutations at nucleotides −25 and −26 and the new HindIII site. The second primer (nucleotides +244 to +266 with respect to the L/ST start site) spans a DraIII site 250 bp downstream from the L/ST start site on the complementary strand. Using pLST-2H as a template, 30 rounds of polymerization should yield a double-stranded DNA fragment 303 bp in length. When this fragment is digested with HindIII and DraIII, it can be cloned into the identical HindIII and DraIII sites of pLST-2H to yield the plasmid PLST-4H which contains all four point mutations. In summary, the nucleotide changes are as follows:

| | | |
|---|---|---|
| TCCAAGCG<u>TATATAT</u>GCGCG | pEBNc3-LAT | wild type |
| TCCAAGC<u>TTGTATAT</u>GCGCG | pLST-2H | phagemid in vitro mutagenesis |
| TCCAAGC<u>TTGTAGGT</u>GCGCG | pLST-4H | PCR-directed mutagenesis |

Prior to introduction of these mutations into the viral genome, their effectiveness with regard to expression of L/STs can be examined on a plasmid template in standard CAT assays. Plasmids can be prepared containing either the wild type or mutated L/ST promoter inserted upstream of the bacterial chloramphenicol acetylase (CAT) gene such that expression of CAT is driven by the promoter when the plasmid is transfected into cells in culture. The level of CAT expression is measured by incubating whole cell extracts obtained from cells so transfected, with a mixture of acetyl CoA and $^{14}$C-labelled chloramphenicol, and then detecting the amount of acetylated chloramphenicol as a measure of the amount of CAT enzyme in the extract. Such methods are standard in the art and are described for example in Sambrook et al. (supra). CAT expression driven by the wild type promoter can be measured and compared with the level of expression driven by the mutated promoter. Promoters which exhibit diminished or background levels of CAT activity can then be introduced into the viral genome in order to generate a viral mutant with altered or abolished L/ST expression.

One example of the generation of a mutated promoter/CAT fusion plasmid is now described although the invention should not be construed as being limited to this construct alone as other mutations may be generated which affect L/ST expression using standard technology available in the art.

The plasmid pWR-CAT contains an intron-less CAT gene and a triple cassette of nucleotides placed just upstream of the polylinker into which the promoter to be tested can be inserted. This triple cassette comprises transcription stop signals designed to prevent spurious CAT expression driven by other regions of the plasmid. The plasmids pEBNc3-LAT (containing the wild type promoter) and pLST-4H (containing the mutated promoter) are digested with NcoI and the resulting 5' overhangs are blunt ended using the Klenow fragment of DNA polymerase I. This DNA is then digested with Ecl136II, which also generates a blunt end. A 957 bp fragment is isolated (nucleotides −935 to +22) and is cloned into the Ecl136II site of pWR-CAT to generate plasmids pLST-CAT (encoding the wild type form of the promoter) and pLST-4H-CAT (encoding the mutated form of the promoter).

B) Introduction of the L/ST mutation into the HSV-1 genome. Because the L/ST promoter is contained entirely within the b repeat sequences of HSV-1, in order to generate a diploid mutant, the mutation must be introduced into both copies of the promoter in the b sequences. This can be accomplished as follows. The virus, 7134, is an ICP0 null mutant, wherein both copies of the ICP0 gene have inserted into them the *E. coli* lacZ gene (encoding β-galactosidase) such that plaques formed by this virus are blue (Cai et al., 1989, J. Virol. 63:4569–4589). A plasmid encoding the L/ST mutation is transfected into cells which are then superinfected with 7134. By the process of homologous recombination, the viral sequences specified in the plasmid recombine into the homologous region in 7134 by the process of homologous recombination. Since this event disrupts the lacZ gene, viral progeny encoding the mutated promoter can be identified by their ability to form white plaques. Stocks of viruses so identified may be propagated on ICP0-expressing cell lines, such as 0–28 cells. To determine whether such viruses encode two copies of a mutated L/ST promoter, DNA is isolated from a plaque purified stock of the virus to be tested and the presence of the mutated L/ST promoter sequences within the disrupted lacZ sequence can be identified by Southern blot hybridization. Viruses encoding the mutated promoter in both copies of the b sequences can be further characterized for their ability to express L/STs by Northern blot analysis of RNA obtained from cells infected with these mutants as described above.

Function of the L/STs. It is known in the art that the region of HSV DNA encoding the L/STs also encodes at least one other gene, i.e., ICP34.5, transcription of which occurs in the opposite direction to that of the L/STs. It is also known that ICP34.5 is non-essential for replication of HSV-1 in tissue culture in that mutants in this gene are replication-competent. Further, it has been reported that this gene plays a role in neurovirulence (Chou et al., 1990, Science 250:1262–1266; Chou et al., 1992, Proc. Natl. Acad. Sci. USA 89:3266–3270). The mutant in ICP34.5 which was used to generate these data is encoded by a region of ICP34.5 which also encodes the L/STs and therefore presumably L/ST expression in cells infected with the mutated ICP34.5 is also disrupted. For this reason, it is unlikely that expression of L/ST is an essential viral function required for replication in tissue culture. The L/STs are most likely to play a role in either the establishment, maintenance or reactivation of virus during the latent phase. Alternatively, they may encode the neurovirulence function attributed to ICP34.5, since the L/STs were also mutated in the generation of the ICP34.5 mutant.

To determine the role played by L/STs in latency, a mutant L/ST virus can first be examined for its ability to replicate in cultured cells of neuronal origin as follows. Neuronal cells are infected with the mutant virus (wild type virus serves as a control) and replication of the virus can be assessed at various times pi using several different criteria, e.g., expression of various viral genes can be monitored by Northern blot hybridization to transcripts of individual viral genes; immunological assays can be used to detect viral protein products; viral DNA replication can be measured; and, most importantly, the production of progeny virus can be assessed in a plaque assay. Each of these techniques is common to any ordinary virologist and any probes or antibodies or other reagents necessary for these experiments are commonly available.

The role played by the L/STs in latency may also be assessed in the mouse eye model. This model is very useful for the study of latency in HSV-1 because spontaneous activation of the lytic cycle in vivo is rare and because there are certain similarities to latent infections in humans (Baichwal et al., 1988, Cell 52:787–789). Essentially, selected numbers of mice are infected in the eye with either wild type virus or an L/ST-minus virus. At various times pi, the mice are sacrificed and their trigeminal ganglia are examined for the presence of reactivatable virus by conventional plaque assay in a cocultivation assay, by in situ hybridization, by extraction of nucleic acid and performing hybridization assays to detect virus specific DNA or RNA, or by immunological assays to detect virus-specific proteins. This technology is commonly used by those skilled in the art and is described for example in Leib et al. (1989, J. Virol. 63:759–768). The role of the L/STs in viral latency will be evident to one skilled in the art of viral latency depending on the results of the experiment. Such an artisan will be able to determine whether L/STs play a role in the establishment or maintenance of the latent state, or in reactivation of the virus from the latent state, depending on when virus is detected in ganglia, whether or not some viral genes are expressed in ganglia, and whether or not virus reactivates from the latent state.

Additional testing of L/ST-minus mutants may be performed using the rabbit eye model as described in Hill et al. (1990, Virology 74:117–125). In this case, rabbits are infected in the eye with wild type or mutant virus and the establishment and/or maintenance of the latent state can be assessed by examining ganglia for the presence or absence of virus and virus-specific products as described above In addition, the ability of virus to reactivate from the latent state can be assessed in vivo following iontophoresis of epinephrine. When rabbits are treated in the eye by iontophoresis for a series of days reactivation of virus was observed (Hill et a, supra).

Should the L/STs be found to encode the neurovirulence factor, for example, then specific regions of the gene which are required for neurovirulence can be identified using a similar type of site-directed mutational analysis as described above for the mutation of the L/ST transcriptional regulatory region. Essentially, small numbers of base pair changes can be made along the length of the neurovirulence gene on a plasmid template. These mutations can be recombined into the viral genome by homologous recombination and progeny viruses so mutated can be tested in any of the models described above.

USE OF THE INVENTION

The compositions and methods of the invention can be used to treat herpes simplex viral diseases in humans. The compositions of the invention include the compounds described contained within a suitable carrier. The compositions and methods can also be used to identify additional compounds that might be useful as therapeutics of herpes simplex viral diseases. While the examples above are directed to HSV-1 gene products, the compositions and methods of the invention are not limited to this virus. As discussed above, the extensive homology between HSV-1 and HSV-2 in the region of DNA encoding L/STs is a strong indication that L/STs are also encoded by HSV-2.

Oligonucleotides encoding sequences which are either in a sense or an antisense orientation with respect to the L/STs may be used to disrupt the function and/or synthesis of the L/STs in virus-infected cells, thereby preventing the virus from (i) establishing a latent state in the host, or (ii) reactivating from the latent state.

Oligonucleotides which can be used in the methods of the invention include any oligonucleotide which inhibits the synthesis of the L/STs in the cell culture assay described below, or which disrupts the function of the L/STs as defined by analysis of the mutant viruses described above. For example, if during the mutational analysis described above, discrete regions of the L/STs appear to be essential for the establishment of or reactivation from latency, these regions would then become primary targets to which oligonucleotides can be directed. Since the sequence of the entire L/STs region is known, synthesis of site-directed oligonucleotides is a simple matter for an ordinary molecular biologist.

Peptides, or fragments thereof, that can be used in the methods of the invention include those that contain an amino acid sequence, or an a analog of an amino acid sequence, contained with any of the ORFs encoded by the L/STs. Antibodies directed against the peptides specified by any of the ORFs encoded by the L/STs, or fragments of such peptides are also useful in the invention and can be used in the methods of the invention in a manner similar to that described for the peptides of the invention.

A simple cell culture assay can be used to determine whether such oligonucleotides, peptides and antibodies, or any other compounds identified according to the methods described above, are capable of inhibiting the synthesis of L/STs. For example, cells, such as NB41A3 cells can be infected with the ICP4 null mutant n12 under the conditions described above such that L/STs would normally be expressed. Either prior to infection or at selected times pi, the oligonucleotide, peptide, antibody or any other compound is added to the culture in a formulation that permits entry of the compound into the cell. Transfection of cells with nucleic acids is common in the art and methods of transfection are described in Sambrook et al. (supra). Similarly, proteins and peptides can be added to cells using the technique of scrape-loading (Fecheimer et al., 1987, Proc. Natl. Acad. Sci. USA 84:8463), or alternatively, certain proteins or peptides can be taken up by cells directly (Frankel et al., 1988, Cell 55:1189; Green et al., 1988, Cell 55:1179; Meek et al., 1990, Nature 343:90). The effect of the compounds on the synthesis of the L/STs can be assessed by determining whether L/STs are synthesized in treated cells as compared with untreated cells. Detection of L/STs can be accomplished by performing Northern blot analysis, or by utilizing PCR technology as described above or as described in any ordinary molecular manual, for example, in Sambrook et al. (supra).

Compounds which inhibit the synthesis of L/STs in the cell culture assay described above can then be tested in vivo for their ability to inhibit either the establishment of latency by HSV, or inhibit reactivation of HSV from the latent state. To determine whether such a compound is capable of inhibiting the establishment of a latent infection by HSV, the compound can be administered to a suitable experimental animal, such as a mouse, either prior to or following infection by HSV. At selected times pi, the animal is sacrificed and the presence or absence of HSV in the ganglia of the mice can be determined by cocultivation of ganglia with permissive cells or by using hybridization and/or PCR technology. Detection of HSV in ganglia is accomplished as described above.

To determine whether a compound is capable of inhibiting reactivation of HSV from the latent state, an experimental animal is infected with HSV such that a latent infection is induced. Two examples of experimental animal models, the mouse eye model and the in vivo rabbit reactivation model are described above. Either before or after infection, the compound in question is administered to the animal in a pharmaceutically acceptable formulation. At selected times post-treatment, ganglia are obtained from the animal and the ability of the virus to reactivate from these ganglia is monitored as described above (the mouse model). Alternatively, virus is induced to reactivate in vivo prior to excision of the ganglia (the rabbit model).

The ability of a compound to inhibit reactivation may also be assessed in the mouse eye model by first establishing a latent viral infection in a select number of mice. Next, the trigeminal ganglia are excised from the mice and are divided into equal groups. Prior to performing the cocultivation assay for reactivation, one group of ganglia is treated with a placebo, i.e., a compound such as isotonic saline which is not known to affect reactivation of the virus. The remaining groups of ganglia are treated with varying concentrations of the test compound. The ability of virus to reactivate from the ganglia in each of the aliquots is then assessed in the cocultivation assay as described in (Leib et al. supra). If the number of viruses which reactivate from ganglia treated with the test compound is less than that from ganglia treated with the placebo, then the test compound is capable of inhibiting or at least reducing the viruses ability to reactivate from the latent state.

The compounds which are capable of inhibiting either establishment of, or reactivation from, the latent state are not limited to oligonucleotides, proteins, peptides or antibodies. The invention also includes any compound capable of disrupting the synthesis or function of the L/STs in the assays described above.

Compounds which are found to inhibit the establishment of or reactivation from the latent state are useful candidate compounds for the treatment of herpes simplex virus disease in humans. Such compounds can be administered to a human in one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). The compounds can be administered to the human in a dosage of 0.1 µg/kg/day to 50 mg/kg/day, either daily or at intervals sufficient to inhibit virus from establishing a latent state or to inhibit virus from reactivating from the latent state, and thus alleviate the long term symptoms of the disease. Precise formulations and dosages may be determined using standard techniques, by a pharmacologist of ordinary skill in the art.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A polypeptide consisting of an amino acid sequence essentially identical to that of the translation product derived from an HSV-specific junction-spanning transcript (L/ST) ORF-1, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

2. A polypeptide consisting of an amino acid sequence essentially identical to that of the translation product derived from an HSV-specific junction-spanning transcript (L/ST) ORF-2, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

3. A polypeptide consisting of an amino acid sequence essentially identical to that of the translation product derived from an HSV-specific junction-spanning transcript (L/ST) ORF-3, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

4. A polypeptide consisting of an amino acid sequence essentially identical to that of the translation product derived from an HSV-specific junction-spanning transcript (L/ST) ORF-4, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

5. The polypeptide of claim 1 being SEQ ID NO:4.
6. The polypeptide of claim 2 being SEQ ID NO:6.
7. The polypeptide of claim 3 being SEQ ID NO:8.
8. The polypeptide of claim 4 being SEQ ID NO:10.
9. A polypeptide consisting of an amino acid sequence essentially identical to that of the translation product derived from an HSV-2-specific junction-spanning transcript (L/ST)

ORF-5, wherein the 5' end of said L/ST maps to the b repeat sequences of HSV-2 DNA at approximately 3 kb and 125 kb, wherein the 3' end of said L/ST extends into the c repeat sequences of HSV-2 DNA and wherein the HSV-2 DNA sequence encoding said L/ST is preceded by an ICP4 binding site and a TATA box.

10. A biologically active L/ST specific polypeptide fragment consisting of an amino acid sequence essentially identical to a fragment of the translation product derived from an HSV-specific junction-spanning transcript (L/ST) ORF-1, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

11. A biologically active L/ST specific polypeptide fragment consisting of an amino acid sequence essentially identical to a fragment of the translation product derived from an HSV-specific junction-spanning transcript (L/ST) ORF-2, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

12. A biologically active L/ST specific polypeptide fragment consisting of an amino acid sequence essentially identical to a fragment of the translation product derived from an HSV-specific junction-spanning transcript (L/ST) ORF-3, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

13. A biologically active L/ST specific polypeptide fragment consisting of an amino acid sequence essentially identical to a fragment of the translation product derived from an HSV-specific junction-spanning transcript (L/ST) ORF-4, wherein the 5' end of said L/ST maps to the b repeat sequences of HSV DNA at approximately 3 kb and 125 kb, wherein the 3' end of said L/ST extends into the c repeat sequences of HSV DNA and wherein the HSV DNA sequence encoding said L/ST is preceded by an ICP4 binding site and a TATA box.

14. A biologically active L/ST specific polypeptide fragment consisting of an amino acid sequence essentially identical to a fragment of the translation product derived from an HSV-2-specific junction-spanning transcript (L/ST) ORF-5, wherein the 5' end of said L/ST maps to the b repeat sequences of HSV-2 DNA at approximately 3 kb and 125 kb, wherein the 3' end of said L/ST extends into the c repeat sequences of HSV-2 DNA and wherein the HSV-2 DNA sequence encoding said L/ST is preceded by an ICP4 binding site and a TATA box.

* * * * *

UNITED STATES PATENT AND TRADEMARK OFFICE
CERTIFICATE OF CORRECTION

PATENT NO. : 5,821,339
DATED : October 13, 1998
INVENTOR(S) : Schaffer, et al

It is certified that error appears in the above-identified patent and that said Letters Patent is hereby corrected as shown below:

Column 6, line 50, delete "(covering 5 pages)" and insert -- , sequentially comprising Figure 10A, Figure 10B, Figure 10C, Figure 10D, and Figure 10E, --

Signed and Sealed this

Ninth Day of March, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:

(A) LENGTH: 39 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Herpes simplex virus
(B) STRAIN: Herpes Simplex Virus Type 1

(xi) SEQUENCE DESCRIPTION: SEQ ID NO:1:

| | | | | |
|---|---|---|---|---|
| TATATATGCG | CGGCTCCTGC | CATCGTCTCT | CCGGAGAGC | 39 |

(2) INFORMATION FOR SEQ ID NO:2:

(i) SEQUENCE CHARACTERISTICS:
(A) LENGTH: 445 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Herpes simplex virus
(B) STRAIN: Herpes Simplex Virus Type 1

(xi) SEQUENCE DESCRIPTION: SEQ ID NO:2:

| | | | | | |
|---|---|---|---|---|---|
| AGGCCTCTTG | CAAGTTTTTA | ATTACCATAC | CCGGAAGTGG | GCGCCCGCCC | AGTGGGCGGT | 60 |
| AGTTACCGCC | CAGTGGGCCG | GCCCGAAGAC | TCGGCGGACG | CTGGTTGGCC | GGGCCCCGCC | 120 |
| GCGCTGGCGG | CCGCCGATTG | GCCAGTCCCG | CCCCCGAGGC | GGCCCGCCCT | GTGAGGGCGG | 180 |
| GCTGGCTCCA | AGCCTATATA | TGCGCGGCTC | CTGCCATCGT | CTCTCCGGAG | AGCGGCTTGG | 240 |
| TGCGGAGCTC | CCGGGAGCTC | CGCGGAAGAC | CCAGGCCGCC | TCGGGTGTAA | CGTTAGACCG | 300 |
| AGTTCGCCGG | GCCGGCTCCG | CGGGCCAGGG | CCCGGGCACG | GGCCTCGGGC | CCCAGGCACG | 360 |
| GCCCGATGAC | CGCCTCGGCC | TCCGCCACCC | GGCGCCGGAA | CCGAGCCCGG | TCGGCCCGCT | 420 |
| CGCGGGCCCA | CGAGCCGCGG | CGCGC | | | | 445 |

(2) INFORMATION FOR SEQ ID NO:3:

(i) SEQUENCE CHARACTERISTICS:
(A) LENGTH: 702 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Herpes simplex virus
(B) STRAIN: Herpes Simplex Virus Type 1

(ix) FEATURE:
(A) NAME/KEY: CDS
(B) LOCATION: 1..702

(xi) SEQUENCE DESCRIPTION: SEQ ID NO:3:

```
ATG  ACC  GCC  TCG  GCC  TCC  GCC  ACC  CGG  CGC  CGG  AAC  CGA  GCC  CGG  TCG         48
Met  Thr  Ala  Ser  Ala  Ser  Ala  Thr  Arg  Arg  Arg  Asn  Arg  Ala  Arg  Ser
 1              5                        10                       15

GCC  CGC  TCG  CGG  GCC  CAC  GAG  CCG  CGG  CGC  GCC  AGG  CGG  GCG  GCC  GAG         96
Ala  Arg  Ser  Arg  Ala  His  Glu  Pro  Arg  Arg  Ala  Arg  Arg  Ala  Ala  Glu
              20                        25                       30

GCC  CAG  ACC  ACC  AGG  TGG  CGC  ACC  CGG  ACG  TGG  GGC  GAG  AAG  CGC  ACC        144
Ala  Gln  Thr  Thr  Arg  Trp  Arg  Thr  Arg  Thr  Trp  Gly  Glu  Lys  Arg  Thr
              35                        40                       45

CGC  GCG  GGG  GTC  GCG  GGG  GTC  GCG  GGG  GTC  GCG  GGG  GTC  GCG  GGG  GTC        192
Arg  Ala  Gly  Val  Ala  Gly  Val  Ala  Gly  Val  Ala  Gly  Val  Ala  Gly  Val
         50                        55                        60

GCG  GGG  GGC  TCC  GGC  GCC  CCC  TCC  CCG  CCC  GCG  CGT  CGC  AGG  CGC  AGG        240
Ala  Gly  Gly  Ser  Gly  Ala  Pro  Ser  Pro  Pro  Ala  Arg  Arg  Arg  Arg  Arg
 65                       70                       75                       80

CGC  GCC  AGG  TGC  TCC  GCG  GTG  ACG  CGC  AGG  CGG  AGG  GCG  AGG  CGC  GGC        288
Arg  Ala  Arg  Cys  Ser  Ala  Val  Thr  Arg  Arg  Arg  Arg  Ala  Arg  Arg  Gly
                   85                        90                       95

GGA  AGG  CGG  AAG  GGG  CGC  GAG  GGG  GGG  TGG  GAG  GGG  TCA  GCC  CCG  CCC        336
Gly  Arg  Arg  Lys  Gly  Arg  Glu  Gly  Gly  Trp  Glu  Gly  Ser  Ala  Pro  Pro
              100                       105                      110

CCC  GGG  CCC  ACG  CCG  GGC  GGT  GGG  GGC  CGG  GGG  CGG  GGG  GCG  GCG  GCG        384
Pro  Gly  Pro  Thr  Pro  Gly  Gly  Gly  Gly  Arg  Gly  Arg  Gly  Ala  Ala  Ala
              115                       120                      125

GTG  GGC  CGG  GCC  TCT  GGC  GCC  GAC  TCG  GGC  GGG  GGG  CTG  TCC  GGC  CAG        432
Val  Gly  Arg  Ala  Ser  Gly  Ala  Asp  Ser  Gly  Gly  Gly  Leu  Ser  Gly  Gln
              130                       135                      140

TCG  TCG  TCA  TCG  TCG  TCG  TCG  GAC  GCG  GAC  TCG  GGA  ACG  TGG  AGC  CAC        480
Ser  Ser  Ser  Ser  Ser  Ser  Ser  Asp  Ala  Asp  Ser  Gly  Thr  Trp  Ser  His
145                      150                       155                      160

TGG  CGC  AGC  AGC  AGC  GAA  CAA  GAA  GGG  GGC  GGC  CCA  CCG  GCG  GGG  GGC        528
Trp  Arg  Ser  Ser  Ser  Glu  Gln  Glu  Gly  Gly  Gly  Pro  Pro  Ala  Gly  Gly
              165                       170                      175

GGC  GGC  GGG  GCG  GCC  GCG  GGC  GCG  CTC  CTG  ACC  GCG  GGT  TCC  GAG  TTG        576
Gly  Gly  Gly  Ala  Ala  Ala  Gly  Ala  Leu  Leu  Thr  Ala  Gly  Ser  Glu  Leu
              180                       185                      190

GGC  GTG  GAG  GTT  ACC  TGG  GAC  TGT  GCG  GTT  GGG  ACG  GCG  CCC  GTG  GGC        624
Gly  Val  Glu  Val  Thr  Trp  Asp  Cys  Ala  Val  Gly  Thr  Ala  Pro  Val  Gly
         195                       200                      205

CCG  GGC  GGC  CGG  GGG  CGG  CGG  GGG  CCG  CGA  TGG  CGG  CGG  CGG  CGG  GCC        672
Pro  Gly  Gly  Arg  Gly  Arg  Arg  Gly  Pro  Arg  Trp  Arg  Arg  Arg  Arg  Ala
     210                       215                       220

ATG  GAG  ACA  GAG  AGC  GTG  CCG  GGG  TGG  TAG                                      702
Met  Glu  Thr  Glu  Ser  Val  Pro  Gly  Trp
225                      230
```

( 2 ) INFORMATION FOR SEQ ID NO:4:

( i ) SEQUENCE CHARACTERISTICS:
        ( A ) LENGTH: 233 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Thr  Ala  Ser  Ala  Ser  Ala  Thr  Arg  Arg  Arg  Asn  Arg  Ala  Arg  Ser
 1              5                        10                       15

Ala  Arg  Ser  Arg  Ala  His  Glu  Pro  Arg  Arg  Ala  Arg  Arg  Ala  Ala  Glu
              20                        25                       30

Ala  Gln  Thr  Thr  Arg  Trp  Arg  Thr  Arg  Thr  Trp  Gly  Glu  Lys  Arg  Thr
```

|  | | | 35 | | | | 40 | | | | | 45 | | |
|---|---|---|---|---|---|---|---|---|---|---|---|---|---|---|
| Arg | Ala | Gly | Val | Ala | Gly | Val | Ala | Gly | Val | Ala | Gly | Val | Ala | Gly | Val |
| | | 50 | | | | | 55 | | | | | 60 | | | |
| Ala | Gly | Gly | Ser | Gly | Ala | Pro | Ser | Pro | Pro | Ala | Arg | Arg | Arg | Arg | Arg |
| 65 | | | | | 70 | | | | | 75 | | | | | 80 |
| Arg | Ala | Arg | Cys | Ser | Ala | Val | Thr | Arg | Arg | Arg | Arg | Ala | Arg | Arg | Gly |
| | | | | 85 | | | | | 90 | | | | | 95 | |
| Gly | Arg | Arg | Lys | Gly | Arg | Glu | Gly | Gly | Trp | Glu | Gly | Ser | Ala | Pro | Pro |
| | | | 100 | | | | | 105 | | | | | 110 | | |
| Pro | Gly | Pro | Thr | Pro | Gly | Gly | Gly | Arg | Gly | Arg | Gly | Ala | Ala | Ala |
| | | | 115 | | | | | 120 | | | | | 125 | | |
| Val | Gly | Arg | Ala | Ser | Gly | Ala | Asp | Ser | Gly | Gly | Gly | Leu | Ser | Gly | Gln |
| | | 130 | | | | | 135 | | | | | 140 | | | |
| Ser | Ser | Ser | Ser | Ser | Ser | Ser | Asp | Ala | Asp | Ser | Gly | Thr | Trp | Ser | His |
| 145 | | | | | 150 | | | | | 155 | | | | | 160 |
| Trp | Arg | Ser | Ser | Ser | Glu | Gln | Glu | Gly | Gly | Gly | Pro | Pro | Ala | Gly | Gly |
| | | | | 165 | | | | | 170 | | | | | 175 | |
| Gly | Gly | Gly | Ala | Ala | Ala | Gly | Ala | Leu | Leu | Thr | Ala | Gly | Ser | Glu | Leu |
| | | | 180 | | | | | 185 | | | | | 190 | | |
| Gly | Val | Glu | Val | Thr | Trp | Asp | Cys | Ala | Val | Gly | Thr | Ala | Pro | Val | Gly |
| | | 195 | | | | | 200 | | | | | 205 | | | |
| Pro | Gly | Gly | Arg | Gly | Arg | Arg | Gly | Pro | Arg | Trp | Arg | Arg | Arg | Ala |
| | | 210 | | | | | 215 | | | | | 220 | | | |
| Met | Glu | Thr | Glu | Ser | Val | Pro | Gly | Trp |
| 225 | | | | | 230 | | | |

( 2 ) INFORMATION FOR SEQ ID NO:5:

( i ) SEQUENCE CHARACTERISTICS:
        ( A ) LENGTH: 87 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Herpes simplex virus
        ( B ) STRAIN: Herpes Simplex Virus Type 1

( i x ) FEATURE:
        ( A ) NAME/KEY: CDS
        ( B ) LOCATION: 1..87

( x i ) SEQUENCE DESCRIPTION: SEQ ID NO:5:

| ATG | GCG | GCG | GCG | GCG | GGC | CAT | GGA | GAC | AGA | GAG | CGT | GCC | GGG | GTG | GTA | 48 |
|---|---|---|---|---|---|---|---|---|---|---|---|---|---|---|---|---|
| Met | Ala | Ala | Ala | Ala | Gly | His | Gly | Asp | Arg | Glu | Arg | Ala | Gly | Val | Val | |
| 1 | | | | 5 | | | | | 10 | | | | | 15 | | |

| GAG | TTT | GAC | AGG | CAA | GCA | TGT | GCG | TGC | AGA | GGC | GAG | TAG | 87 |
|---|---|---|---|---|---|---|---|---|---|---|---|---|---|
| Glu | Phe | Asp | Arg | Gln | Ala | Cys | Ala | Cys | Arg | Gly | Glu | | |
| | | | 20 | | | | 25 | | | | | | |

( 2 ) INFORMATION FOR SEQ ID NO:6:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Ala Ala Ala Ala Gly His Gly Asp Arg Glu Arg Ala Gly Val Val
 1               5                   10                  15

Glu Phe Asp Arg Gln Ala Cys Ala Cys Arg Gly Glu
                 20                  25

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Herpes simplex virus
        ( B ) STRAIN: Herpes Simplex Virus Type 1

( i x ) FEATURE:
        ( A ) NAME/KEY: CDS
        ( B ) LOCATION: 1..30

( x i ) SEQUENCE DESCRIPTION: SEQ ID NO:7:

ATG GAG ACA GAG AGC GTG CCG GGG TGG TAG                                    30
Met Glu Thr Glu Ser Val Pro Gly Trp
 1               5                   10

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Met Glu Thr Glu Ser Val Pro Gly Trp
 1               5

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Herpes simplex virus
        ( B ) STRAIN: Herpes Simplex Virus Type 1

( i x ) FEATURE:
        ( A ) NAME/KEY: CDS
        ( B ) LOCATION: 1..45

( x i ) SEQUENCE DESCRIPTION: SEQ ID NO:9:

ATG TGC GTG CAG AGG CGA GTA GTG CTT GCC TGT CTA ACT CGC TAg                45
Met Cys Val Gln Arg Arg Val Val Leu Ala Cys Leu Thr Arg
 1               5                   10

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:10:

Met Cys Val Gln Arg Arg Val Val Leu Ala Cys Leu Thr Arg
  1                5                        10

(2) INFORMATION FOR SEQ ID NO:11:

(i) SEQUENCE CHARACTERISTICS:
        (A) LENGTH: 12001 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Herpes simplex virus
        (B) STRAIN: Herpes Simplex Virus Type 1

(xi) SEQUENCE DESCRIPTION: SEQ ID NO:11:

```
AGGCCTCTTG  CAAGTTTTTA  ATTACCATAC  CGGGAAGTGG  GCGGCCCGGC  CCATTGGGCG     60
GTAACTCCCG  CCCAATGGGC  CGGGCCCCGA  AGACTCGGCG  GACGCTGGTT  GGCCGGGCCC    120
CGCCGCGCTG  GCGGCCGCCG  ATTGGCCAGT  CCCGCCCCCG  AGGCGGCCCG  CCCTGTGAGG    180
GCGGGCTGGC  TCCAAGCGTA  TATATGCGCG  GCTCCTGCCA  TCGTCTCTCC  GGAGAGCGGC    240
TTGGTGCGGA  GCTCCCGGGA  GCTCCGCGGA  AGACCCAGGC  CGCCTCGGGT  GTAACGTTAG    300
ACCGAGTTCG  CCGGGCCGGC  TCCGCGGGCC  AGGGCCCGGG  CACGGGCCTC  GGGCCCCAGG    360
CACGGCCCGA  TGACCGCCTC  GGCCTCCGCC  ACCCGGCGCC  GGAACCGAGC  CCGGTCGGCC    420
CGCTCGCGGG  CCCACGAGCC  GCGGCGCGCC  AGGCGGGCGG  CCGAGGCCCA  GACCACCAGG    480
TGGCGCACCC  GGACGTGGGG  CGAGAAGCGC  ACCCGCGCGG  GGGTCGCGGG  GGTCGCGGGG    540
GTCGCGGGGG  TCGCGGGGGT  CGCGGGGGGC  TCCGGCGCCC  CCTCCCCGCC  CGCGCGTCGC    600
AGGCGCAGGC  GCGCCAGGTG  CTCCGCGGTG  ACGCGCAGGC  GGAGGGCGAG  GCGCGGCGGA    660
AGGCGGAAGG  GGCGCGAGGG  GGGGTGGGAG  GGGTCAGCCC  CGCCCCCCGG  GCCCACGCCG    720
GGCGGTGGGG  GCCGGGGGCG  GGGGCGGCG   GCGGTGGGCC  GGGCCTCTGG  CGCCGACTCG    780
GGCGGGGGGC  TGTCCGGCCA  GTCGTCGTCA  TCGTCGTCGT  CGGACGCGGA  CTCGGGAACG    840
TGGAGCCACT  GGCGCAGCAG  CAGCGAACAA  GAAGGCGGGG  GCCCACCGGC  GGGGGGCGGC    900
GGCGGGGCGG  CCGCGGGCGC  GCTCCTGACC  GCGGGTTCCG  AGTTGGGCGT  GGAGGTTACC    960
AGGGACTGTG  CGGTTGGGAC  GGCGCCCGTG  GGCCCGGGCG  GCCGGGGGCG  GCGGGGGCCG   1020
CGATGGCGGC  GGCGGCGGGC  CATGGAGACA  GAGAGCGTGC  CGGGGTGGTA  GAGTTTGACA   1080
GGCAAGCATG  TGCGTGCAGA  GGCGAGTAGT  GCTTGCCTGT  CTAACTCGCT  AGTCTCGGCC   1140
GCGGGGGGCC  CGGGCTGCCC  GCCGCCACCG  CTTTAAAGGG  CCGCGCGCGA  CCCCCGGGGG   1200
GTGTGTTTTG  GGGGGGGCCC  GTTTTCGGCG  TCTGGCCGCT  CCTCCCCCCG  CTCCTCCCCC   1260
```

| | | | | | | |
|---|---|---|---|---|---|---|
| CGCTCCTCCC | CCCGCTCCTC | CCCCCGCTCC | TCCCCCCGCT | CCTCCCCCCG | CTCCTCCCCC | 1320 |
| CGCTCCTCCC | CCCGCTCCTC | CCCCCGCTCC | TCCCCCCGCT | CCTCCCCCCG | CTCCTCCCCC | 1380 |
| CGCTCCTCCC | CCCGCTCCTC | CCCCCGCTCC | TCCCCCCGCT | CCTCCCCCCG | CTCCTCCCCC | 1440 |
| CGCTCCTCCC | CCCGCTCCCG | CGGCCCCGCC | CCCACGCCC | GCCGCGCGCG | CGCACGCCGC | 1500 |
| CCGGACCGCC | GCCCGCCTTT | TTTGCGCGCG | CGCGCGCCCG | CGGGGGGCCC | GGGCTGCCAC | 1560 |
| AGGTGAAACC | AACAGAGCAC | GGCGCACTCC | GCACGTCACA | CGTCACGTCA | TCCACCACAC | 1620 |
| CTGCCCAACA | ACACAACTCA | CAGCGACAAC | TCACCGCGCA | ACAACTCCTG | TTCCTCATCC | 1680 |
| ACACGTCACC | GCGCACCTCC | CGCTCCTCCA | GACGTACCCC | GGCGCAACAC | ACCGCTCCTG | 1740 |
| CTACACACCA | CCGCCCCCTC | CCCAGCCCCA | GCCCTCCCCA | GCCCAGCCC | TCCCGGCCC | 1800 |
| CAGCCCTCCC | CGGCCCCAGC | CCTCCCCGGC | CCCAGCCCTC | CCCGGCCCA | GCCCTCCCCG | 1860 |
| GCCCCAGCCC | TCCCGGCCC | CAGCCCTCCC | CGGCGCGTCC | CGCGCTCCCT | CGGGGGGGTT | 1920 |
| CGGGCATCTC | TACCTCAGTG | CCGCCAATCT | CAGGTCAGAG | ATCCAAACCC | TCCGGGGGCG | 1980 |
| CCCGCGCACC | ACCACCGCCC | CTCGCCCCCT | CCCGCCCCTC | GCCCCTCCC | GCCCCTCGCC | 2040 |
| CCCTCCCGCC | CCTCGCCCCC | TCCCGCCCCT | CGCCCCCTCC | CGCCCCTCGC | CCCCTCCCGC | 2100 |
| CCCTCGCCCC | CTCCCGCCCC | TCGCCCCCTC | CCGCCCCTCG | CCCCCTCCCG | CCCCTCGCCC | 2160 |
| CCTCCCGCCC | CTCGCCCCCT | CCCGCCCCTC | GCCCCCTCCC | GCCCCTCGCC | CCCTCCCGCC | 2220 |
| CCTCGCCCCC | TCCCGCCCCT | CGCCCCCTCC | CGCCCCTCGC | CCCCTCCCGC | CCCTCGCCCC | 2280 |
| CTCCCGCCCC | TCGCCCCCTC | CCGCCCCTCG | CCCCCTCCCG | CCCCTCGAAT | AAACAACGCT | 2340 |
| ACTGCAAAAC | TTAATCAGGT | TGTTGCCGTT | TATTGCGTCT | TCGGGTCTCA | CAAGCGCCCC | 2400 |
| GCCCCGTCCC | GGCCCGTTAC | AGCACCCCGT | CCCCCTCGAA | CGCGCCGCCG | TCGTCTTCGT | 2460 |
| CCCAGGCGCC | TTCCCAGTCC | ACAACTTCCC | GCCGCGGGGG | CGTGGCCAAG | CCCGCCTCCG | 2520 |
| CCCCCAGCAC | CTCCACGGCC | CCCGCCGCCG | CCAGCACGGT | GCCGCTGCGG | CCCGTGGCCG | 2580 |
| AGGCCCAGCG | AATCCCGGGC | GGCGCCGGCG | GCAGGGCCCC | CGGGCCGTCG | TCGTCGCCGC | 2640 |
| GCAGCACCAG | CGGGGGGGCG | TCGTCGTCGG | GCTCCAGCAG | GGCGCGGGCG | CAAAAGTCCC | 2700 |
| TCCGCGGCCC | GCGCCACCGG | GCCGGGCCGG | CGCGCACCGC | CTCGCGCCCC | AGCGCCACGT | 2760 |
| ACACGGGCCG | CAGCGGCGCG | CCCAGGCCCC | AGCGCGCGCA | GGCGGCGTGC | GAGTGGGCCT | 2820 |
| CCTCCTCGCA | GAAGTCCGGC | GCGCCGGGCG | CCATGGCGTC | GGTGGTCCCC | GAGGCCGCCG | 2880 |
| CCCGGCCGTC | CAGCGCCGGC | AGCACGGCCC | GGCGGTACTC | GCGCGGGGAC | ATGGGCACCG | 2940 |
| GCGTGTCCGG | GCCGAAGCGC | GTGCGCACGC | GGTAGCGCAC | GTTGCCGCCG | CGGCACAGGC | 3000 |
| GCAGCGGCGG | CGCGTCGGGG | TACAGGCGCG | CGTGCGCGGC | CTCCACGCGC | GCGAAGACCC | 3060 |
| CCGGGCCGAA | CACGCGGCCC | GAGGCCAGCA | CCGTGCGGCG | CAGGTCCCGC | GCCGCCGGCC | 3120 |
| AGCGCACGGC | GCACTGCACG | GCGGGCAGCA | GCTCGCACGC | CAGGTAGGCG | TGCTGCCGCG | 3180 |
| ACACCGCGGG | CCCGTCGGCG | GGCCAGTCGC | AGGCGCGCAC | GGTGTTGACC | ACGATGAGCC | 3240 |
| GCCGGTCGCC | GGCGCTGGCG | AGCAGCCCCA | GAAACTCCAC | GGCCCCGGCG | AAGGCCAGGT | 3300 |
| CCCGCGTGGA | CAGCAGCAGC | ACGCCCTGTG | CGCCCAGCGC | CGACACGTCG | GGGGCGCCGG | 3360 |
| TCCAATTGCC | CGCCCAGGCG | GCCGTGTCCG | GCCGCACAG | CCGGTTGGCC | AGGGCCGCCA | 3420 |
| GCAGGCAGGA | CAGCCCGCCG | CGCTCGGCGG | ACCACTCCGG | CGGCCCCCC | GAGGCCCCGC | 3480 |
| CGCCGGCCAG | GTCCTCGCCC | GGCAGCGGCG | AGTACAGCAC | CACCACGCGC | ACGTCCTCGG | 3540 |
| GGTCGGGGAT | CTGGCGCATC | CAGGCCGCCA | TGCGGCGCAG | CGGGCCCGAG | GCGCGCAGGG | 3600 |
| GGCCAAAGAG | GCGGCCCCCG | GCGGCCCCGT | GGGGGTGGGG | GTTATCGTCG | TCGTCGCCGC | 3660 |

| | | | | | | |
|---|---|---|---|---|---|---|
| CGCCGCACGC | GGCCTGGGCG | GCGGGGGCGG | GCCCGGCGCA | CCGCGCGGCG | ATCGAGGCCA | 3720 |
| GGGCCCGCGG | GTCAAACATG | AGGGCCGGTC | GCCAGGGGAC | GGGGAACAGC | GGGTGGTCCG | 3780 |
| TGAGCTCGGC | CACGGCGCGC | GGGGAGCAGT | AGGCCTCCAG | GGCGGCGGCC | GCGGGCGCCG | 3840 |
| CCGTGTGGCT | GGGCCCCGGG | GGCTGCCGCC | GCCAGCCGCC | CAGGGGGTCG | GGGCCCTCGG | 3900 |
| CGGGCCGGCG | CGACACGGCC | ACGGGGCGCG | GGCGGGCCTG | CGCCGCGGCG | GCCCGGGGCG | 3960 |
| CCGCGGGCTG | GGCGGGGGCG | GGCTCGGGCC | CCGGGGGCGT | GGAGGGGGGC | GCGGGCGCGG | 4020 |
| GGAGGGGGGC | GCGGGCGTCC | GAGCCGGGGG | CGTCCGCGCC | GCTCTTCTTC | GTCTTCGGGG | 4080 |
| GTCGCGGGCC | GCCGCCTCCG | GGCGGCCGGG | CCGGGCCGGG | ACTCTTGCGC | TTGCGCCCCT | 4140 |
| CCCGCGGCGC | GGCGGAGGCG | GCGGCGGCCG | CCAGCGCGTC | GGCGGCGTCC | GGTGCGCTGG | 4200 |
| CCGCCGCCGC | CAGCAGGGGG | CGCAGGCTCT | GGTTGTCAAA | CAGCAGGTCC | GCGGCGGCGG | 4260 |
| CGGCCGCGGA | GCTCGGCAGG | CGCGGGTCCC | GCGGCAGCGC | GGGGCCCAGG | GCCCCGGCGA | 4320 |
| CCAGGCTCAC | GGCGCGCACG | GCGGCCACGG | CGGCCTCGCT | GCCGCCGGCC | ACGCGCAGGT | 4380 |
| CCCCGCGCAG | GCGCATGAGC | ACCAGCGCGT | CGCGCACGAA | CCGCAGCTCG | CGCAGCCACG | 4440 |
| CGCGCAGGCG | GGGCGCGTCG | GCGTGCGGCG | GCGGCGGGGA | AGCGGGGCCC | GCGGGTCCCT | 4500 |
| CCGGCCGCGG | GGGGCTGGCG | GGCCGGGCCC | CGGCCAGCCC | CGGGACGGCC | GCCAGGTCGC | 4560 |
| CGTCGAAGCC | CTCGGCCAGC | GCCTCCAGGA | TCCCGCGGCA | GGCGGCCAGG | CACTCGACGG | 4620 |
| CCACGCGGCC | GGCCTGGGCG | CGGCGCCCGG | CGTCGTCGTC | GGCGTCGGCG | TGGCGGGCGG | 4680 |
| CGTCGGGGTC | GTCGCCCCCC | GCGGGGGAGG | CGGGCGCGGC | GGACAGCCGC | CCCAGGCGGC | 4740 |
| GAGGATCCCC | GCGGCGCCGT | ACCCGGCGGG | CACCGCGCGC | TCGCCCGGTG | CGGCGGCGGC | 4800 |
| GACGGCGGCG | ACCCCCTCGT | CATCTGCGCC | GGCGCCGGGG | CTCCCCGCGG | CCCCCGTCAG | 4860 |
| CGCCGCGTTC | TCGCGCGCCA | ACAGGGGCGC | GTAGGCGCGG | CGCAGGCTGG | TCAGCAGGAA | 4920 |
| GCCCTTCTGC | GCGCGGTCGT | ATCGGCGGCT | CATGGCCACG | GCGGCCGCCG | CGTGCGCCAG | 4980 |
| GCCCCAGCCG | AAGCGGCCGG | CCGCCATGGC | GTAGCCCAGG | TGGGGCACGG | CCCGCGCCAC | 5040 |
| GCTGCCGGTG | ATGAAGGAGC | TGCTGTTGCG | CGCGGCGCCC | GAGATCCGGA | AGCAGGCCTG | 5100 |
| GTCCAGCGCC | ACGTCCCCGG | GGACCACGCG | CGGGTTCTGG | AGCCACCCCA | TGGCCTCCGC | 5160 |
| GTCCGGGGTG | TACAGCAGCC | GCGTGATCAG | GGCGTACTGC | TGCGCGGCGT | CGCCCAGCTC | 5220 |
| GGGCGCCCAC | ACGGCCGCCG | GGGCGCCCGA | GGCCTCGAAC | CGGCGTCGCG | CCTCCTCCGC | 5280 |
| CTCGGGCGCC | CCCCAGAGGC | CCGGGCGGCT | GTCGCCCAGG | CCGCCGTACA | GCACCCGCCC | 5340 |
| CGGGGGCGGG | GGCCCGGCGC | CGGGCCACGG | CTCCCCGCTG | ACGTACCCGT | CGCGATAGCG | 5400 |
| CGCGTAGAAG | GCGCCGGAGG | TCGCGTCGGC | GTCCAGCTCG | ACCCGCCGGG | GCTGCCCGGC | 5460 |
| CGTGAAGCGG | CCCGTGGCGT | CGCGGCCGGC | CACCGCCGCG | CGGGCCCGGC | GGCGCTCGAT | 5520 |
| GCGGCCCGCG | GAGGCCGCGG | GGGTCCTCGC | CGCCGCCCGG | GGCTTGGGCG | CGGCCTCGGA | 5580 |
| GAGGGGGGGT | GGCCCGGGCG | GGGGCGGCGT | CCGCCCGGGG | GCTGCCGGCG | CCGCGCTCGA | 5640 |
| CGGACCCCGC | CCGACGGCCC | GCGCCTCGCG | TGCGTGGTCG | GCCGCGTCGT | TGCCGTCGTC | 5700 |
| GTCCTCGTCC | TCGTCGGACG | ACGAGGACGA | AGAGGATGCG | GACGACGAGG | ACGAGGACCC | 5760 |
| GGAGTCCGAC | GAGGTCGATG | ACGCCGATGG | CCGCCACCGG | CCGTGACGAC | GTCTCCGCGG | 5820 |
| CGGCTGGGCC | GGCGGGCGCG | GCGACAGGCG | GTCCGTGGGG | TCCGGATACG | CGCCGCGTAG | 5880 |
| CGGGGCCTCC | CGTTCGCGGC | CCCGGGCCGG | GCCCGGTCG | CCGGCGGCGT | CGGCTGCGTC | 5940 |
| GTCGTACTCG | TCCCCGTCAT | CGTCGTCGGC | TCGAAAGGCG | GGGTCCGGG | GCGGCGAGGC | 6000 |
| CGCGGGGTCG | GGCGTCGGGA | TCGTCCGGAC | GGCCTCCTCT | ACCATGGAGG | CCAGCAGAGC | 6060 |

| | | | | | | |
|---|---|---|---|---|---|---|
| CAGCTGTCGC | GGCGAGACGG | CGTCCCCGGC | GTCCTCGCCG | GCGTCGGTGC | CCGCCGCGGG | 6120 |
| GGCCCTCCCG | TCCCGCCGGG | CGTCGTCGAG | GTCGTGGGGG | TGGTCGGGGT | CGTGGTCGGG | 6180 |
| GTCGTCCCCG | CCCTCCTCCG | TCTCCGCGCC | CCACCCGAGG | GCCCCCCCCT | CGTCGCGGTC | 6240 |
| TGGGCTCGGG | GTGGGCGGCG | GCCCGTCGGT | GGGGCCCGGG | GAGCCGGGGC | GCTGCTTGTT | 6300 |
| CTCCGACGCC | ATCGCCGATG | CGGGGCGATC | CTCCGGGGAT | ACGGCTGCGA | CGGCGGACGT | 6360 |
| AGCACGGTAG | GTCACCTACG | GACTCTCGAT | GGGGGGAGGG | GGCGAGACCC | ACGGACCCCG | 6420 |
| ACGACCCCG | CCGTCGACGC | GGAACTAGCG | CGGACCGGTC | GATGCTTGGG | TGGGAAAAAG | 6480 |
| GACAGGGACG | GCCGATCCCC | CTCCCGCGCT | TCGTCCGCGT | ATCGGCGTCC | CGGCGCGGCG | 6540 |
| AGCGTCTGAC | GGTCTGTCTC | TGGCGGTCCC | GCGTCGGGTC | GTGGATCCGT | GTCGGCAGCC | 6600 |
| GCGCTCCGTG | TGGACGATCG | GGGCGTCCTC | GGGCTCATAT | AGTCCCAGGG | GCCGGCGGGA | 6660 |
| AGGAGGAGCA | GCGGAGGCCG | CCGGCCCCC | GCCCCCCGG | CGGGCCCACC | CCGAACGGAA | 6720 |
| TTCCATTATG | CACGACCCCG | CCCCGACGCC | GGCACGCCGG | GGGCCCGTGG | CCGCGGCCCG | 6780 |
| TTGGTCGAAC | CCCCGGCCCC | GCCCATCCGC | GCCATCTGCC | ATGGGCGGGG | CGCGAGGGCG | 6840 |
| GGTGGGTCCG | CGCCCCGCCC | CGCATGGCAT | CTCATTACCG | CCCGATCCGG | CGGTTTCCGC | 6900 |
| TTCCGTTCCG | CATGCTAACG | AGGAACGGGC | AGGGGCGGG | GCCCGGGCCC | CGACTTCCCG | 6960 |
| GTTCGGCGGT | AATGAGATAC | GAGCCCCGCG | CGCCCGTTGG | CCGTCCCCGG | GCCCCCCGGT | 7020 |
| CCCGCCCGCC | GGACGCCGGG | ACCAACGGGA | CGGCGGGCGG | CCCAAGGGCC | GCCCGCCTTG | 7080 |
| CCGCCCCCC | ATTGGCCGGC | GGGCGGGACC | GCCCCAAGGG | GGCGGGGCCG | CCGGGTAAAA | 7140 |
| GAAGTGAGAA | CGCGAAGCGT | TCGCACTTCG | TCCAATATA | TATATATTAT | TAGGGCGAAG | 7200 |
| TGCGAGCACT | GGCGCCGTGC | CCGACTCCGC | GCCGGCCCCG | GGGCGGGCC | CGGGCGGCGG | 7260 |
| GGGGCGGGTC | TCTCCGGCGC | ACATAAAGGC | CCGGCGCGAC | CGACGCCCGC | AGACGGCGCC | 7320 |
| GGCCACGAAC | GACGGGAGCG | GCTGCGGAGC | ACGCGGACCG | GGAGCGGGAG | TCGCAGAGGG | 7380 |
| CCGTCGGAGC | GGACGGCGTC | GGCATCGCGA | CGCCCCGGCT | CGGGATCGGG | ATCGCATCGG | 7440 |
| AAAGGGACAC | GCGGACGCGG | GGGGAAAGA | CCCGCCCACC | CCACCCACGA | AACACAGGGG | 7500 |
| ACGCACCCCG | GGGGCCTCCG | ACGACAGAAA | CCCACCGGTC | CGCCTTTTTT | GCACGGGTAA | 7560 |
| GCACCTTGGG | TGGGCGGAGG | AGGGGGGGAC | GCGGGGGCGG | AGGAGGGGGG | ACGCGGGGGC | 7620 |
| GGAGGAGGGG | GGACGCGGGG | GCGGAGGAGG | GGGACGCGG | GGGCGGAGGA | GGGGGACGC | 7680 |
| GGGGGCGGAG | GAGGGGCTC | ACCCGCGTTC | GTGCCTTCCC | GCAGGAGGAA | CGTCCTCGTC | 7740 |
| GAGGCGACCG | GCGGCGACCG | TTGCGTGGAC | CGCTTCCTGC | TCGTCGGGCG | GGGGGAAGCC | 7800 |
| ACTGTGGTCC | TCCGGGACGT | TTTCTGGATG | GCCGACATTT | CCCCAGGCGC | TTTTGCGCCT | 7860 |
| TGTGTAAAAG | CGCGGCGTCC | CGCTCTCCGA | TCCCCGCCCC | TGGGCACGCG | CAAGCGCAAG | 7920 |
| CGCCCTTCCC | GCCCCCTCTC | ATCGGAGTCT | GAGGTAGAAT | CCGATACAGC | CTTGGAGTCT | 7980 |
| GAGGTCGAAT | CCGAGACAGC | ATCGGATTCG | ACCGAGTCTG | GGACCAGGA | TGAAGCCCCC | 8040 |
| CGCATCGGTG | GCCGTAGGGC | CCCCCGGAGG | CTTGGGGGGC | GGTTTTTCT | GGACATGTCG | 8100 |
| GCGGAATCCA | CCACGGGGAC | GGAAACGGAT | GCGTCGGTGT | CGGACGACCC | CGACGACACG | 8160 |
| TCCGACTGGT | CTTATGACGA | CATTCCCCCA | CGACCCAAGC | GGGCCCGGGT | AAACCTGCGG | 8220 |
| CTCACGAGCT | CTCCCGATCG | GCGGGATGGG | GTTATTTTTC | CTAAGATGGG | GCGGGTCCGG | 8280 |
| TCTACCCGGG | AAACGCAGCC | CCGGGCCCCC | ACCCCGTCGG | CCCCAAGCCC | AAATGCAATG | 8340 |
| CTACGGCGCT | CGGTGCGCCA | GGCCCAGAGG | CGGAGCAGCG | CACGATGGAC | CCCCGACCTG | 8400 |
| GGCTACATGC | GCCAGTGTAT | CAATCAGCTG | TTTCGGGTCC | TGCGGGTCGC | CCGGGACCCC | 8460 |

| | | | | | | |
|---|---|---|---|---|---|---|
| CACGGCAGTG | CCAACCGCCT | GCGCCACCTG | ATACGCGACT | GTTACCTGAT | GGGATACTGC | 8520 |
| CGAGCCCGTC | TGGCCCCGCG | CACGTGGTGC | CGTTTGCTGC | AGGTGTCCGG | CGGAACCTGG | 8580 |
| GGCATGCACC | TGCGCAACAC | CATACGGGAG | GTGGAGGCTC | GATTCGACGC | CACCGCGGAA | 8640 |
| CCCGTGTGCA | AGCTTCCTTG | TTTGGAGACC | AGACGGTACG | GCCCGGAGTG | TGATCTTAGT | 8700 |
| AATCTCGAGA | TTCATCTCAG | CGCGACAAGC | GATGATGAAA | TCTCCGATGC | CACCGATCTG | 8760 |
| GAGGCCGCCG | GTTCGGACCA | CACGCTCGCG | TCCCAGTCCG | ACACGGAGGA | TGCCCCCTCC | 8820 |
| CCCGTTACGC | TGGAAACCCC | AGAACCCCGC | GGGTCCCTCG | CTGTGCGTCT | GGAGGATGAG | 8880 |
| TTTGGGGAGT | TTGACTGGAC | CCCCCAGGAG | GGCTCCCAGC | CCTGGCTGTC | TGCGGTCGTG | 8940 |
| GCCGATACCA | GCTCCGTGGA | ACGCCCGGGC | CCATCCGATT | CTGGGGCGGG | TCGCGCCGCA | 9000 |
| GAAGACCGCA | AGTGTCTGGA | CGGCTGCCGG | AAAATGCGCT | TCTCCACCGC | CTGCCCCTAT | 9060 |
| CCGTGCAGCG | ACACGTTTCT | CCGGCCGTGA | GTCCGGTCGC | CCCGACCCCC | TTGTATGTCC | 9120 |
| CCAAAATAAA | AGACCAAAAT | CAAAGCGTTT | GTCCCAGCGT | CTTAATGGCG | GGAAGGGCGG | 9180 |
| AGAGAAACAG | ACCACGCGGA | CATGGGGGGT | GTTTGGGGGT | TTATTGGCAC | CGGGGGCTAA | 9240 |
| AGGGTGGTAA | CCGGATAGCA | GATGTGAGGA | AGTCGGGGCC | GTTCGCCGCG | AACGGCGATC | 9300 |
| AGAGGGTCAG | TTTCTTGCGG | ACCACGGCCC | GGCGATGTGG | GTTGCTCGTC | TGGGACCTCG | 9360 |
| GGCATGCCCA | TACACGCACA | ACACGGACGC | CGCACCGGAT | GGGACGTCGT | AAGGGGGCCT | 9420 |
| GGGGTAGCTG | GGTGGGGTTT | GTGCAGAGCA | ATCAGGGACC | GCAGCCAGCG | CATACAATCG | 9480 |
| CGCTCCCGTC | CGTTTGTCCC | GGGCAGTACC | ACGCCGTACT | GGTATTCGTA | CCGGCTGAGC | 9540 |
| AGGGTCTCCA | GGGGGTGGTT | GGGGGCCGCG | GGGAACGGGG | TCCACGCCAC | GGTCCACTCG | 9600 |
| GGCAAAAACC | GAGTCGGCAC | GGCCCACGGT | TCTCCCACCC | ACGCGTCTGG | GGTCTTGATG | 9660 |
| GCGATAAATC | TTACCCCGAG | CCGGATTTTT | TGGGCGTATT | CGAGAAACGG | CACACACAGA | 9720 |
| TCCGCCGCGC | CTACCACCCA | CAAGTGGTAG | AGGCGAGGGG | GGCTGGGTTG | GTCTCGGTGC | 9780 |
| AGCAGTCGGA | AGCACGCCAC | GGCGTCCACG | ACCTCGGTGC | TCTCCAAGGG | GCTGTCCTCC | 9840 |
| GCAAACAGGC | CCGTGGTGGT | GTTTGGGGGG | CAGCGACAGG | ACCTAGTGCG | CACGATCGGG | 9900 |
| CGGGTGGGTT | TGGGTAAGTC | CATCAGCGGC | TCGGCCAACC | GTCGAAGGTT | GGCCGGACGA | 9960 |
| ACGACGACCG | GGGTACCCAG | GGGTTCTGAT | GCCAAAATGC | GGCACTGCCT | AAGCAGGAAG | 10020 |
| CTCCACAGGG | CCGGGCTTGC | GTCGACGGAA | GTCCGGGGCA | GGGCGTTGTT | CTGGTCAAGG | 10080 |
| AGGGTCATTA | CGTTGACGAC | AACAACGCCC | ATGTTGGTAT | ATTACAGGCC | CGTGTCCGAT | 10140 |
| TTGGGGCACT | TGCAGATTTG | TAAGGCCACG | CACGGCGGGG | AGACAGGCCG | ACGCGGGGC | 10200 |
| TGCTCTAAAA | ATTTAAGGGC | CCTACGGTCC | ACAGACCCGC | CTTCCCGGGG | GGGCCCTTGG | 10260 |
| AGCGACCGGC | AGCGGAGGCG | TCCGGGGGAG | GGGAGGGTGA | TTTACGGGGG | GGTAGGTCAG | 10320 |
| GGGGTGGGTC | GTCAAACTGC | CGCTCCTTAA | AACCCCGGGG | CCCGTCGTTC | GGGGTGCTCG | 10380 |
| TTGGTTGGCA | CTCACGGTGC | GGCGAATGGC | CTGTCGTAAG | TTTTGTCGCG | TTTACGGGGG | 10440 |
| ACAGGGCAGG | AGGAAGGAGG | AGGCCGTCCC | GCCGGAGACA | AAGCCGTCCC | GGGTGTTTCC | 10500 |
| TCATGGCCCC | TTTTATACCC | CAGCCGAGGA | CGCGTGCCTG | GACTCCCCGC | CCCCGGAGAC | 10560 |
| CCCCAAACCT | TCCCACACCA | CACCACCCAG | CGAGGCCGAG | CGCCTGTGTC | ATCTGCAGGA | 10620 |
| GATCCTTGCC | CAGATGTACG | GAAACCAGGA | CTACCCCATA | GAGGACGACC | CCAGCGCGGA | 10680 |
| TGCCGCGGAC | GATGTCGACG | AGGACGCCCC | GGACGACGTG | GCCTATCCGG | AGGAATACGC | 10740 |
| AGAGGAGCTT | TTTCTGCCCG | GGGACGCGAC | CGGTCCCCTT | ATCGGGGCCA | ACGACCACAT | 10800 |
| CCCTCCCCCG | TGTGGCGCAT | CTCCCCCCGG | TATACGACGA | CGCAGCCGGG | ATGAGATTGG | 10860 |

-continued

| | | | | | | |
|---|---|---|---|---|---|---|
| GGCCACGGGA | TTTACCGCGG | AAGAGCTGGA | CGCCATGGAC | AGGGAGGCGG | CTCGAGCCAT | 10920 |
| CAGCCGCGGC | GGCAAGCCCC | CCTCGACCAT | GGCCAAGCTG | GTGACTGGCA | TGGGCTTTAC | 10980 |
| GATCCACGGA | GCGCTCACCC | CAGGATCGGA | GGGGTGTGTC | TTTGACAGCA | GCCATCCAGA | 11040 |
| TTACCCCCAA | CGGGTAATCG | TGAAGGCGGG | GTGGTACACG | AGCACGAGCC | ACGAGGCGCG | 11100 |
| ACTGCTGAGG | CGACTGGACC | ACCCGGCGAT | CCTGCCCCTC | CTGGACCTGC | ATGTCGTCTC | 11160 |
| CGGGGTCACG | TGTCTGGTCC | TCCCCAAGTA | CCAGGCCGAC | CTGTATACCT | ATCTGAGTAG | 11220 |
| GCGCCTGAAC | CCACTGGGAC | GCCCGCAGAT | CGCAGCGGTC | TCCCGGCAGC | TCCTAAGCGC | 11280 |
| CGTTGACTAC | ATTCACCGCC | AGGGCATTAT | CCACCGCGAC | ATTAAGACCG | AAAATATTTT | 11340 |
| TATTAACACC | CCCGAGGACA | TTTGCCTGGG | GGACTTTGGC | GCCGCGTGCT | TCGTGCAGGG | 11400 |
| TTCCCGATCA | AGCCCCTTCC | CCTACGGAAT | CGCCGGAACC | ATCGACACCA | ACGCCCCGA | 11460 |
| GGTCCTGGCC | GGGGATCCGT | ATACCACGAC | CGTCGACATT | TGGAGCGCCG | GTCTGGTGAT | 11520 |
| CTTCGAGACT | GCCGTCCACA | ACGCGTCCTT | GTTCTCGGCC | CCCCGCGGCC | CCAAAAGGGG | 11580 |
| CCCGTGCGAC | AGTCAGATCA | CCCGCATCAT | CCGACAGGCC | CAGGTCCACG | TTGACGAGTT | 11640 |
| TTCCCCGCAT | CCAGAATCGC | GCCTCACCTC | GCGCTACCGC | TCCCGCGCGG | CCGGGAACAA | 11700 |
| TCGCCCGCCG | TACACCCGAC | CGGCCTGGAC | CCGCTACTAC | AAGATGGACA | TAGACGTCGA | 11760 |
| ATATCTGGTT | TGCAAAGCCC | TCACCTTCGA | CGGCGCGCTT | CGCCCCAGCG | CCGCAGAGCT | 11820 |
| GCTTTGTTTG | CCGCTGTTTC | AACAGAAATG | ACCGCCCCT | GGGGCGGTG | CTGTTTGCGG | 11880 |
| GTTGGCACAA | AAAGACCCCG | ATCCGCGTCT | GTGGTGTTTT | TGGCATCATG | TCGCAGGGCG | 11940 |
| CCATGCGTGC | CGTTGTTCCC | ATTATCCCAT | TCCTTTTGGT | TCTTGTCGGT | GTATCGGGGG | 12000 |
| T | | | | | | 12001 |

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Herpes simplex virus
        ( B ) STRAIN: Herpes Simplex Virus Type 1

( x i ) SEQUENCE DESCRIPTION: SEQ ID NO:12:

| | | |
|---|---|---|
| CGCGCCGCGG | CTCGTGGG | 18 |

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Herpes simplex virus (B) STRAIN: Herpes Simplex Virus Type 1

(xi) SEQUENCE DESCRIPTION: SEQ ID NO:13:

TCCAAGCGTA TATATGCGCG 20

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Herpes simplex virus
(B) STRAIN: Herpes Simplex Virus Type 1

(xi) SEQUENCE DESCRIPTION: SEQ ID NO:14:

TCCAAGCTTG TATATGCGCG 20

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Herpes simplex virus
(B) STRAIN: Herpes Simplex Virus Type 1

(xi) SEQUENCE DESCRIPTION: SEQ ID NO:15:

TCCAAGCTTG TAGGTGCGCG 20